US011821863B2

United States Patent
Fischer et al.

(10) Patent No.: US 11,821,863 B2
(45) Date of Patent: Nov. 21, 2023

(54) SYSTEM AND METHOD FOR DETECTING STRUCTURAL CHANGE OF A MOLECULE OR ITS ENVIRONMENT WITH NMR SPECTROSCOPY

(71) Applicant: Bruker BioSpin GmbH, Rheinstetten (DE)

(72) Inventors: Christian Fischer, Rheinstetten (DE); Michael Bernstein, Leics (GB); Michael Erich Wilhelm Fey, Andover, MA (US); Ian Michael Clegg, Widnes (GB)

(73) Assignee: Bruker BioSpin GmbH, Rheinstetten (DE)

( * ) Notice: Subject to any disclaimer, the term of this patent is extended or adjusted under 35 U.S.C. 154(b) by 358 days.

(21) Appl. No.: 17/248,591

(22) Filed: Jan. 29, 2021

(65) Prior Publication Data
US 2021/0262957 A1  Aug. 26, 2021

(30) Foreign Application Priority Data
Feb. 20, 2020 (EP) .................................... 20158623

(51) Int. Cl.
*G01N 24/08* (2006.01)
(52) U.S. Cl.
CPC ................................. *G01N 24/087* (2013.01)
(58) Field of Classification Search
CPC .................................................... G01N 24/087
USPC ........................................................ 324/309
See application file for complete search history.

(56) References Cited

PUBLICATIONS

Arbogast, Luke W., et.al., "Mapping Monoclonal Antibody Structure by 2D 13C NMR at Natural Abundance," Analytical Chemistry 87, 7 (2015): 3556-3561.
European Search Report for Application No. 20158623.7, dated Aug. 26, 2020, 10 pages.
Amezcua, Carlos A., et al., "Assessment of Higher Order Structure Comparability in Therapeutic Proteiins Using Nuclear Magnetic Resonance Spectroscopy", Journal of Pharmaceutical Sciences, vol. 102, No. 6, Jun. 2013, pp. 1724-1733.
Buchner, Lena, et al., "Peakmatch: a Simple and Robust Method for Peak List Matching", J Biomol NMR 55; DOI 10.1007/s10858-013-9708-z, 2013, pp. 267-277.
Japelj, Bostjan, et al., "Biosimilar Structural Comparability Assessment by NMR: From Small Proteins to Monoclonal Antibodies", Scientific Reports; 6:32201; DOI: 10.1038/srep32201, 2016, 12 pages.

*Primary Examiner* — Steven L Yeninas
*Assistant Examiner* — Rahul Maini
(74) *Attorney, Agent, or Firm* — Brake Hughes Bellermann LLP

(57) ABSTRACT

A system, method and computer program product for detecting indicators for structural changes of NMR active test molecules in a test sample, or indicators for structural changes of the environment of said test molecules in relation to a reference molecule. Initial local similarity values are obtained, using a similarity function and representing a local similarity between a reference spectrum and a test spectrum within corresponding similarity regions (SRR, SRT). The initial local similarity values represent a similarity map (SM1) in which contours of a first shape type are indicators (I1) for structural changes of the test molecule, and in which contours of a second shape type are indicators (I2) for structural changes of the environment of said test molecule in relation to the reference molecule.

20 Claims, 13 Drawing Sheets

SYSTEM AND METHOD FOR DETECTING STRUCTURAL CHANGE OF A MOLECULE OR ITS ENVIRONMENT WITH NMR SPECTROSCOPY

CROSS REFERENCE TO RELATED APPLICATION

This application claims the benefit of priority based on European Application No. EP20158623.7, filed on Feb. 20, 2020 and entitled "System and method for detecting structural change of a molecule or its environment with NMR spectroscopy," the entirety of which is hereby incorporated by reference.

TECHNICAL FIELD

The present description generally relates to signal detection in NMR spectroscopy and more particularly to signal changes of signal peaks in multidimensional NMR spectra to detect deviations of a test molecule from a reference molecule.

BACKGROUND

Nuclear magnetic resonance (NMR) spectroscopy is a spectroscopic technique to observe local magnetic fields around atomic nuclei. A sample is placed in a magnetic field and the NMR signal is produced by excitation of the nuclei sample with radio frequency (RF) pulses into nuclear magnetic resonance, which is detected with sensitive RF receivers. The intramolecular magnetic field around an atom in a molecule changes the resonance frequency, thus giving access to details of the electronic structure of a molecule and its individual functional groups. For example, NMR spectroscopy is used to identify monomolecular organic compounds, proteins and other complex molecules. Besides identification, NMR spectroscopy provides detailed information about the structure, dynamics, reaction state, and chemical environment of molecules. Thereby, the term structure of a molecule is used in that it refers to all levels of protein structure including primary to quaternary structure. Common types of NMR are proton and carbon-13 NMR spectroscopy, but it is applicable to any kind of sample that contains nuclei possessing spin.

Upon excitation of the sample with a radio frequency (typically 60-1200 MHz) pulse, a nuclear magnetic resonance response is obtained which is referred to as free induction decay (FID) herein. The FID is a very weak signal and requires sensitive RF receivers to pick up. A Fourier transform can be applied to extract the frequency-domain spectrum from the raw time-domain FID. A spectrum from a single FID typically has a low signal-to-noise ratio. Decay times of the excitation, typically measured in seconds, depend on the effectiveness of relaxation, which is faster for lighter nuclei and in solids, and slower for heavier nuclei and in solutions whereas they can be very long in gasses.

Two-dimensional nuclear magnetic resonance spectroscopy (2D NMR) is a set of nuclear magnetic resonance spectroscopy (NMR) methods which give data plotted in a space defined by two frequency axes rather than one. Types of 2D NMR include correlation spectroscopy (COSY), J-spectroscopy, exchange spectroscopy (EXSY), and nuclear Overhauser effect spectroscopy (NOESY). Two-dimensional NMR spectra provide more information about a molecule than one-dimensional NMR spectra and are especially useful in determining the structure of a molecule, particularly for molecules that are too complicated to work with using one-dimensional NMR. Each experiment consists of a sequence of radio frequency (RF) pulses with delay periods in between them. The timing, frequencies, and intensities of these pulses distinguish different NMR experiments from one another. The two dimensions of a two-dimensional NMR experiment are two frequency axes with each representing a chemical shift. Each frequency axis is associated with one of the two time variables, which are the length of the evolution period (the evolution time) and the time elapsed during the detection period (the detection time). They are each converted from a time series to a frequency series through a two-dimensional Fourier transform. It is to be noted, that even three-dimensional or even higher dimensional NMR spectra can be obtained by using a corresponding number of time variables in the NMR experiment.

Biologics are biopharmaceuticals, e.g., proteins, vaccines, mAbs (monoclonal Antibodies). These molecules have an intricate folded, three-dimensional shape. Their spatial structure and dynamics of proteins are responsible for their function. Four structural levels define the spatial structure, often referred to as "Higher Order Structure" (HOS).

Primary structure: Describes the atomic composition and the chemical bonds between these atoms.

Secondary structure: Describes local segments, e.g., $\alpha$-helix, $\beta$-sheet, etc.

Tertiary structure: Describes the entire 3D structure of the molecule: every atom has its defined position.

Quaternary structure: Describes the 3D structure of the aggregated biopolymer

For example, two n-dimensional NMR spectra are useful to validate the molecular structure of a test substance with regards to a reference substance because the respective NMR signal positions are very sensitive to the 3D structure of the substances. If, for example, the three-dimensional structure of proteins in the test substance has changed in comparison to a corresponding reference substance, one or more peaks in the NMR test spectrum obtained from the test substance are shifted in relation to a corresponding NMR reference spectrum of the reference substance. In cases where proteins of the test substance are aggregated (agglutinated), a broadening of respective peaks in the NMR test spectrum occurs in comparison with the corresponding peaks in the NMR reference spectrum. In other words, changes in peak positions between a reference spectrum and a test spectrum indicate changes in the spatial structure HOS of the test substance in relation to the reference substance. That is, the analysis of the test spectrum provides insights into the quality of the test substance in comparison with the reference substance. For example, the analyzed proteins may form the active ingredients of a pharmaceutical product. The NMR reference spectrum thereby may reflect a three-dimensional structure of the proteins which is proven for a high effectiveness of treatment. Any deviation from this reference structure may result in a lower effectiveness. Changes in the molecular structure may be caused, for example, by bad transport or storage conditions to which the test substance was exposed. It is therefore a goal to detect in the test substance deviations from the molecular structure of the reference substance. This can be achieved by analyzing peak shifts and peak broadenings in the NMR test spectra.

Known methods in the field are the so-called Combined Chemical Shift Deviation (CCSD) and a method called ECHOS-NMR to assess higher order structure (HOS) comparability in protein samples.

SUMMARY

There is therefore a need to provide systems and methods for reliable detection of deviations of the molecular structure of a test substance from a reference substance. Thereby, the term molecular structure refers to all levels of protein structure including the primary to quaternary structures, as well as the structure of the environment of the molecule (i.e. dynamic effects and aggregation).

This technical problem is solved by the features of the independent claims providing, in one embodiment, a computer-implemented method for detecting indicators for structural changes of NMR active test molecules in a test sample, and/or indicators for structural changes of the environment of said test molecules in relation to a reference molecule. In case that both types of structural changes are present in the test molecule, the method can identify both types and also distinguishes between the two types. However, it is not necessary that both types are present in the test sample. The method also detects such structural changes in case only one type (stricter change of molecule or environment) is present in the test sample. A further embodiment is a computer program product with instructions that, when read into a memory of a computer system and being executed by at least one processor of the computer system, causes the computer system to execute said method. A further embodiment is directed to said computer system.

The method starts with obtaining an n-dimensional NMR reference spectrum associated with the reference molecule having a known spatial structure, and further obtaining an n-dimensional NMR test spectrum associated with the test molecule having an unknown spatial structure. Typically, the test sample is a substance which is supposed to correspond to the reference substance. However, the test sample may have undergone some treatment (e.g., particular handling or storage conditions of the test substance) which may have caused some damage to the original molecule structure or the molecule's environment structure. Structural changes of the environment of the test molecules include aggregation and dynamic effects which are well known by a person skilled in the art of NMR spectrum analysis. The reference spectrum is typically obtained from a corresponding reference spectrum database which includes NMR spectra obtained from reference molecules with the ideal structure of the molecule. The test spectrum may be obtained from a database which is used to store test spectra obtained from NMR experiments for samples including test molecules of said test substance, or may be obtained directly as the output of such an NMR experiment. To allow a meaningful comparison of the two spectra, the reference spectrum RS and the test spectrum TS have the same spectral resolution and the same spectral range. That is, each spectrum point of the reference spectrum RS has a corresponding spectrum point in the test spectrum TS, where the corresponding spectrum points have the same coordinates in each dimension of the spectrum. For example, in case the test and reference spectra are two-dimensional spectra, two corresponding spectrum points have exactly the same position within the respective spectrum planes of the test spectrum and the reference spectrum.

For the further processing of the two spectra a subset of spectrum points of the reference spectrum may be selected. This subset may correspond to all spectrum points of the spectrum or may include only a particular portion of the reference spectrum comprising NMR signals which are characteristic of the reference molecule. Of course, the selected subset of reference spectrum points automatically implies a corresponding subset of test spectrum points in the test spectrum.

For each selected spectrum point of the reference spectrum the following operations are processed in a corresponding loop:

In the reference spectrum, a first similarity region is selected. The first similarity region surrounds the currently processed spectrum point in the test spectrum. Thereby, the currently processed spectrum point may be located at the center of mass of the similarity region. The similarity region may have an arbitrary shape. For example, in two-dimensional terminology, a square, a rectangle, a circle, an ellipse or any other appropriate shape of the similarity region may be chosen. In an n-dimensional spectrum with n>2 the respective geometric objects (e.g., cuboids, ellipsoids, etc.) may be used to define the n-dimensional similarity region. The similarity regions selected different for different spectrum points may differ in size and shape. Advantageously, the size of a particular similarity region having an overlap with a particular NMR signal peak in the reference spectrum is of the order of the full width half maximum of the particular peak in each dimension of the peak.

In the test spectrum, a corresponding second similarity region is selected which surrounds the corresponding spectrum point in the test spectrum. That is, the spectrum points covered by the second similarity region in the test spectrum have the same coordinates as the corresponding spectrum points covered by the first similarity region in the reference spectrum.

The term similarity region, as used herein, describes corresponding sections of the two spectra which are used to compute a similarity between the two spectra for the currently processed spectrum point. This is achieved by using a similarity function to compute an initial local similarity value for the currently processed spectrum point. The initial local similarity value represents the local similarity between the reference spectrum and the test spectrum within the corresponding similarity regions. That is, the initial local similarity for the currently processed spectrum point goes beyond a simple comparison of corresponding spectrum points in the reference and test spectra but takes into account the entire spectrum information around the currently process spectrum point as defined by the respective similarity region.

Advantageously, the similarity function is one of a Pearson correlation function, cosine similarity function or modified cosine similarity function, Euclidian distance, Manhattan distance, Minkowski distance, local norm ratio.

Once the initial local similarity value is computed for the currently processed spectrum point, the next spectrum point is selected for processing until all spectrum points of the selected subset have been processed. Thereby, the order in which the spectrum points are selected is irrelevant.

The initial local similarity values represent a similarity map in which contours of a first shape type are indicators for structural changes, and in which contours of a second shape type are indicators for structural changes of the environment of said test molecule in relation to the reference molecule. For example, in the case of two-dimensional spectra the first shape type typically corresponds to wave-shaped contours whereas the second shape type may correspond to sink-shaped or peak-shaped contours dependent on the selected representation.

In other words, the indicators for structural changes of the test molecule (contours of the first shape type) reflect shifted NMR signal peaks of the test spectrum when compared with the reference spectrum. It is known that test NMR peaks which occur at a different position than in the reference spectrum are caused by such structural changes of the molecule. This also includes such peaks which have completely disappeared in the test spectrum, as well as such peaks that only appear in the text spectrum. The indicators for structural changes of the environment of said test molecule (contours of the second shape type) reflect broadened NMR signal peaks of the test spectrum when compared with the reference spectrum. It is known that test NMR peaks which occur at the same position as in the reference spectrum but with a broadened shape of the peak amplitudes are caused by said structural changes of the molecule's environment which may be related to the effect of aggregation or to dynamic effects.

The computed initial local similarity values may be visualized as said similarity map for a user. Such a representation is advantageous in that the computed similarity map only includes contour structures where NMR peaks of the test spectrum are either broadened or shifted with regards to the reference spectrum. The similarity map has no contours where NMR peaks of the test spectrum correspond to those of the reference spectrum. That is, the similarity map only represents change indicators associated with NMR signal peaks in the test spectrum which show changes with regards to the peaks in the reference spectrum. Unchanged parts of the spectrum are suppressed. This effect is caused by taking into account the entire similarity region when computing the local similarity values with the similarity function. In other words, because the similarity only shows deviations of the test spectrum from the reference spectrum, non-deviating parts in the test spectrum cause no indicators in the similarity map. In other words, the computer system compares the spectrum obtained from the test sample with the spectrum of the reference sample with the result that only peaks of the test spectrum which deviate from peaks in the reference spectrum are represented by corresponding indicators in the similarity map. Thereby, indicators for broadened peaks have a different shape than indicators for shifted peaks. Therefore, a person skilled in NMR spectrum analysis can use a visualization of the similarity map to easily differentiate peaks changes caused by a structural change of the test molecule from peak changes caused by structural changes of the molecule's environment.

In one embodiment, the method includes further steps which allow to filter out such change indicators which are associated with structural changes of the molecule itself. Only indicators which relate to structural changes of the environment of the molecule are kept. The additional steps of this embodiment are performed as a sub-loop (or inner loop) within the loop (or outer loop) over of the selected spectrum points. Once the initial local similarity value is determined for the currently processed spectrum point, a predefined shifting region is projected on the corresponding spectrum point in the test spectrum. The shape of the predefined shifting region defines a subset of spectrum points in the reference spectrum to which the similarity region in the test spectrum is to be shifted in the various iterations of the sub-loop. For each shifted similarity region, a local similarity value with the similarity region of the reference spectrum is determined, referred to as the shifted local similarity value. In more detail, for all spectrum points within the predefined shifting region of the test spectrum, the following actions are performed:

shifting the second similarity region (of the test spectrum) to a further spectrum point of the shifting region;

computing, by using the similarity function, a shifted local similarity value representing the local similarity between the reference spectrum in the first similarity region and the test spectrum in the shifted similarity region; and determining the spectrum point within the predefined shifting region showing the maximum shifted local similarity value.

Once the maximum shifted local similarity values have been determined for all selected spectrum points (i.e., once the outer loop has been completely processed), the determined maximum shifted local similarity values represent an environment similarity map in which contours of a third shape type are indicators for structural changes of the environment of said test molecule in relation to the reference molecule. The indicators for structural changes of the molecule itself are eliminated from the environment similarity map.

That is, the environment similarity map facilitates the detection of change indicators for the structural changes of the environment of the molecule which may relate to dynamic effects or to aggregation. The filtered environment similarity map allows an analysis of the NMR result which is less error prone because it provides to the user a map where the user can immediately identify NMR signal peaks associated with said environment changes via the contours of the third shape type and potential confusion with change indicators representing structural changes is excluded. As multi-dimensional NMR spectra of molecules with weights in the order of 150 kDalton typically include a huge number of NMR signal peaks which are sometimes arranged in very dense clusters, the herein disclosed method allows to quickly and reliably identify a subset of peaks in the test spectrum which provides information about deviations of the test sample from the reference sample.

In one embodiment, the environment similarity map can be further improved in the sense that an NMR spectrum analyst can even more reliably identify such relevant peaks with regards to environmental changes. In this embodiment, a spectrum difference value is computed for each spectrum point of the selected subset (in the outer loop) by computing a difference between respective amplitudes in the reference spectrum and the test spectrum.

The determined maximum shifted local similarity values are then multiplied with the respective spectrum difference values to obtain an improved environment similarity map. In the improved environment similarity map, only peaks which are broadened in the test spectrum in comparison with respective peaks of the reference spectrum, appear as clearly shaped contours in the improved environment similarity map which can be easily and reliably identified by a human user of the system to quickly identify dynamic effects or aggregation for the test substance.

In a further embodiment, the method is extended with a filter to emphasize indicators for structural changes of the molecule. In this embodiment, indicators for structural changes of the environment are not entirely eliminated but they are largely suppressed so that the detection of structural changes of the molecule with regards to a reference molecule can be easily and reliably identified by a human user. To achieve this, a similarity increase value is computed for each spectrum point of the selected subset of spectrum points (i.e. all spectrum points processed in the outer loop) as the difference between the respective initial local similarity value and the respective maximum local shifted similarity value. Thereby, the similarity increase values represent a structural change similarity map in which contours of the first shape type are indicators for structural change of the test molecule in relation to the reference molecule (i.e. indicators for peak shifts). This structural change similarity map still includes indicators for broadened peaks. However, such indicators are very small compared to the first shape type indicators. The first shape type can be compared to a kind of wave form.

The structural change similarity map can further be improved by using the multiplication with a difference spectrum similarly as already described for the improved environment similarity map. Again, a spectrum difference value is computed for each spectrum point of the subset by computing a difference between respective amplitudes in the reference spectrum and the test spectrum. It is to be noted that, in case the embodiment for generating the improved environment similarity map is already implemented, this step does not to be executed again but the result of the earlier computation can be used. The similarity increase values are then multiplied with the respective spectrum difference values to obtain an improved structural change similarity map.

Further aspects will be realized and attained by means of the elements and combinations particularly depicted in the appended claims. It is to be understood that both, the foregoing general description and the following detailed description are exemplary and explanatory only, and are not restrictive.

DETAILED DESCRIPTION

Figure 1A:
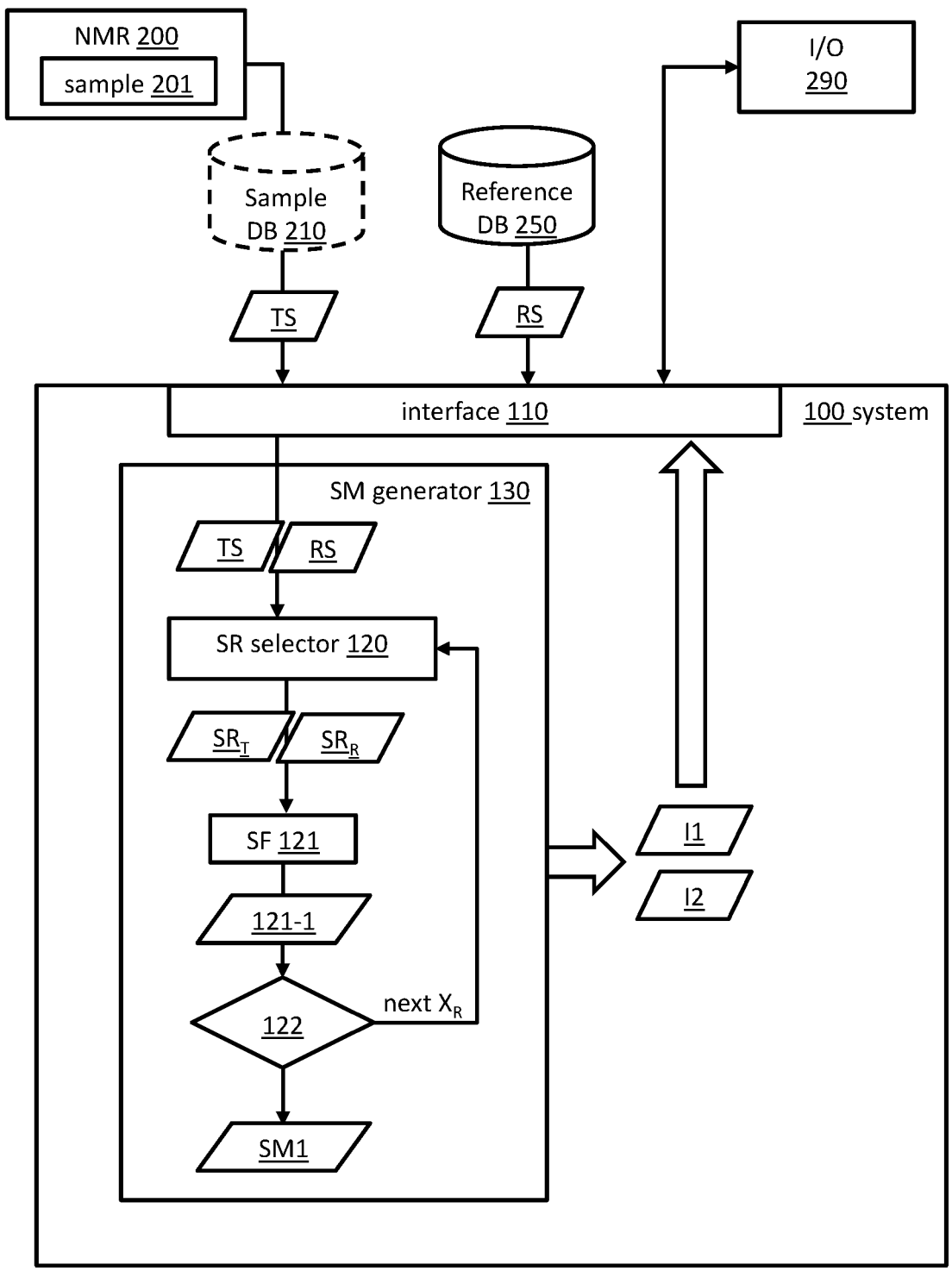
FIG. 1A includes a block diagram of a computer system for detecting indicators for structural changes associated with NMR active test molecules in relation to a reference molecule using a similarity map generator module according to an embodiment.
Figure 2:
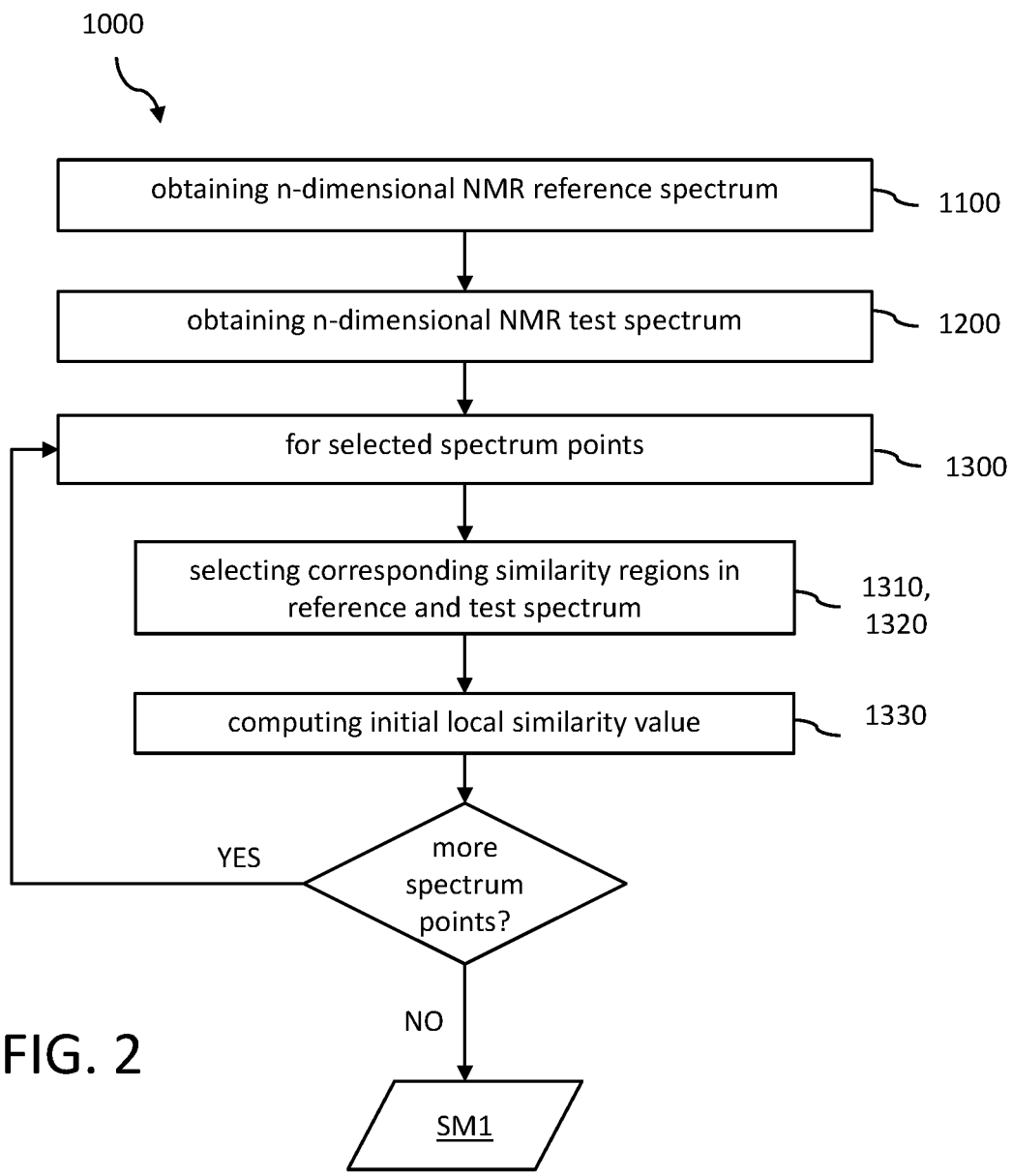
FIG. 2 is a simplified flow chart of a computer-implemented method for detecting indicators for structural changes associated with NMR active test molecules in relation to a reference molecule according to an embodiment.

FIG. 1A illustrates a block diagram of a computer system 100 for detecting indicators for structural changes associated with NMR active test molecules in relation to a reference molecule using a similarity map (SM) generator module 130 according to an example embodiment. The computer system 100 has a memory and one or more processors to process modules of a computer program which includes instructions, that when processed by the computer system, perform the steps of a computer implemented method 1000 as depicted in the flowchart of FIG. 2. For this reason, FIG. 1A is described in the context of FIG. 2 and corresponding reference numbers can refer to FIG. 1A as well as to FIG. 2. The system 100 has input/output means 290 which allow a human user to interact with the system. For example, results provided by the system, such as for example indicator I1, I2, may be presented to a user via a respective display device. The I/O means 290 may also be used by a user to provide certain parameters to the system to influence the graphical presentation. For example, threshold levels for noise filtering or the like may be specified by user via the I/O means 290.

Initially, the system 100 obtains 1100 an n-dimensional NMR reference spectrum RS associated with the reference molecule having a known spatial structure via the interface 110. Typically, the reference spectrum RS is provided by a corresponding reference database 250 which is communicatively coupled with the system 100. The reference DB 250 may also be an integral component of the system 100. Further, via the interface 110, the system 100 obtains 1200 an n-dimensional NMR test spectrum TS associated with the test molecule which is included in the test sample. Typically, a test sample 201 includes a large quantity of test molecules and an NMR spectrum obtained from the test sample 201 reflects an averaged NMR response of all test molecules in the test sample which are affected by the radio frequency pulse applied by the respective NMR equipment 200. The spatial structure of such test molecules is however unknown at the point in time when the NMR experiment is performed. The reference spectrum RS and the test spectrum TS have the same spectral resolution and the same spectral range. In other words, both spectra have been obtained from NMR experiments under comparable conditions. It is not relevant when the test spectrum has been obtained. For example, it may already pre-exist in a corresponding sample database 210, or it may be directly obtained as an output from the NMR equipment 200 which is used for performing the NMR experiment. As can be seen in the two-dimensional example of FIGS. 3A, 3B, each spectrum point of the reference spectrum RS has a corresponding spectrum point in the test spectrum TS, and corresponding spectrum points $X_R$, $X_T$ have therefore the same coordinates $x_1$, $x_2$. The same is true for any higher dimensional NMR spectrum example.

The received spectra are then provided as an input to the SM generator 130. The SM generator processes 1300, for at least a subset of spectrum points of the reference spectrum SR, the following operations in a loop. As mentioned above, the subset(s) of spectrum points may include all spectrum points or it may include only spectrum points in the vicinity of particular peaks of the test spectrum, or it may include only points within a predefined spectrum range (e.g., only spectrum points within the spectrum range inside the edge zone border line 300.

A similarity region (SR) selector module 120 selects 1310, in the reference spectrum RS, a first similarity region $SR_R$ surrounding the currently processed spectrum point (referred to as $X_R$), and further selects 1320, in the test spectrum TS, a corresponding second similarity region $SR_T$ surrounding the corresponding spectrum point (referred to as $X_T$) in the test spectrum TS. That is, the first and second similarity regions cover the same spectrum points in that they cover a spectrum region with the same coordinates in both spectra. In general, the similarity region may have any shape/size which fits in the reference spectrum and shape/size of the similarity region may vary with every spectrum point.

Figure 3A:
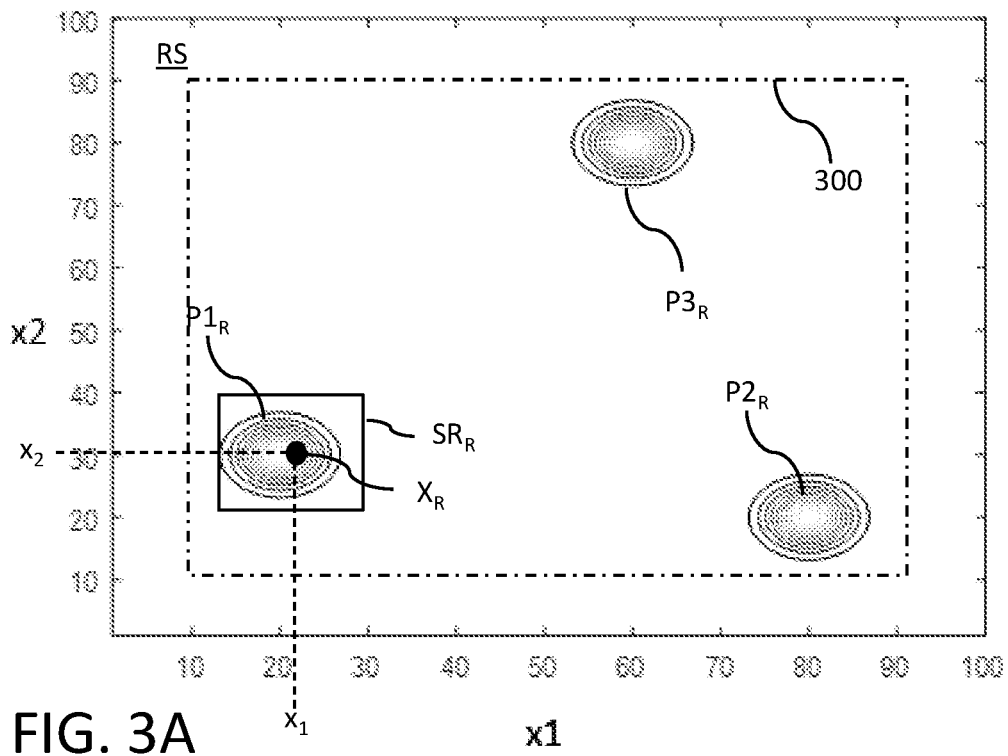
FIGS. 3A, 3B illustrate an example of a two-dimensional reference spectrum and a corresponding test spectrum, each with three NMR signal peaks.
Figure 3B:
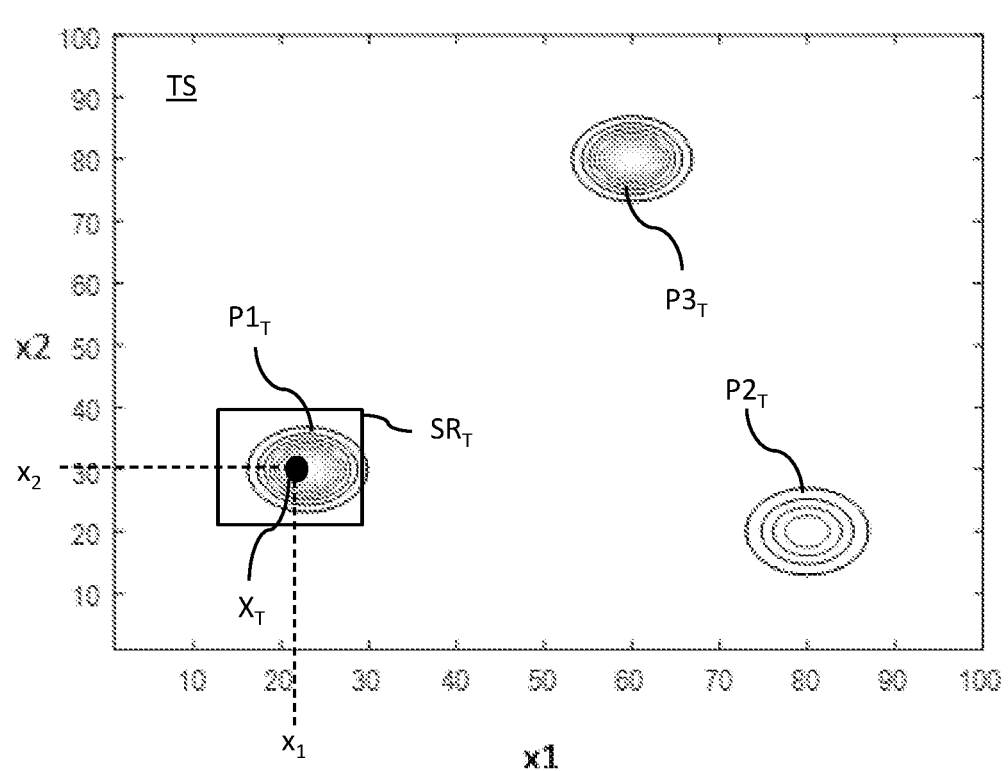

Turning briefly to FIGS. 3A and 3B, FIG. 3A illustrates the first similarity region $SR_R$ as a rectangle which surrounds the currently processed spectrum point $X_R$ in the two dimensional example reference spectrum RS with the dimensions x1, x2. It is to be noted that the shape of the similarity region can be chosen as any region around the currently processed spectrum point which is suitable to determine a similarity measure for the similarity of corresponding portions of the reference and test spectra in the spatial vicinity of the currently processes spectrum point. That is, in the two dimensional example, a square, a circle or an elliptic shape may be used instead of the rectangular shape of the example. In FIG. 3A, three example peaks $P1_R$, $P2_R$, $P3_R$ are shown in the reference spectrum RS. Typically, the extensions of such peaks in each dimension are different. In the example, peaks are a bit broader in the x1 dimension than in the x2 dimension. Therefore, it can be advantageous to use a shape where the extensions of the similarity in different dimensions also varies. A rectangular shape which is broader in the x1 dimension than in the x2 dimension may be better suited to compare the similarity of spectrum regions around the example peaks than a square or circular shape.

In an advantageous embodiment, spectrum points which are located in an edge zone with a distance from the border line of the spectrum corresponding to at least half the width of the similarity region in the respective spectrum dimension are not considered for the subset of spectrum points to be processed by the SM generator. The edge zone in FIG. 3A for the similarity region $SR_R$ is the area between the border of the reference spectrum RS and the edge zone border line 300. For such points within the edge zone, the similarity region would actually go beyond the borders of the spectrum leading to less meaningful similarity values when comparing test and reference spectrum.

In an advantageous embodiment, in spectrum regions where peaks are present, the size of a particular similarity region may be chosen to have an overlap with a particular NMR signal peak in the reference spectrum in the order of the full width half maximum of the particular peak in each dimension of the peak. That is, it is not necessary that the similarity region remains the same for all spectrum points. Rather, the size of the similarity region may be adapted to the width of respective spectrum peaks in the various dimensions. As a consequence, the SM generator may use similarity regions which are smaller for narrow peaks than for broad peaks. The computation effort for computing the local similarity values increases with the number of spectrum points contained in the similarity region. Thus, adapting the size of the similarity regions to the respective peak widths can save computing resources while still maintaining a high accuracy level for the local similarity values. An optional peak size analyser module may be used to determine typical peak sizes in the obtained reference spectrum during an initialization step and annotate the peaks accordingly. Such annotations may be used by the SM generator to dynamically adapt the size of the similarity regions when processing spectrum points in the vicinity of the annotated peaks. However, it is also possible to use a predefined similarity region size for all selected spectrum points which may be adapted to the broadest peaks occurring in the reference spectrum.

In FIG. 3B showing the test spectrum TS, also three peaks $P1_T$, $P2_T$, $P3_T$ are shown. It is apparent that the test sample does not exactly correspond to the reference sample because the peaks show differences. Although $P3_T$ corresponds exactly to $P3_R$, $P1_T$ differs from $P1_R$ in it is slightly shifted to the right in the x1 dimension, and $P2_T$ differs from $P2_R$ in that it is broadened. The second similarity $SR_T$ in the test spectrum corresponds to the first similarity region $SR_R$ in the reference spectrum RS (cf. FIG. 3A) in that it has the same shape (and size) and is covering the same spectrum coordinates while surrounding the spectrum point $X_T$ (which has the same coordinates $x_1$, $x_2$ as the corresponding spectrum point $X_R$ in the reference spectrum TR). The shift of $P1_T$ in view of $P1_R$ becomes clearly visible when comparing the position of both peaks in the respective similarity regions.

Figure 4A:
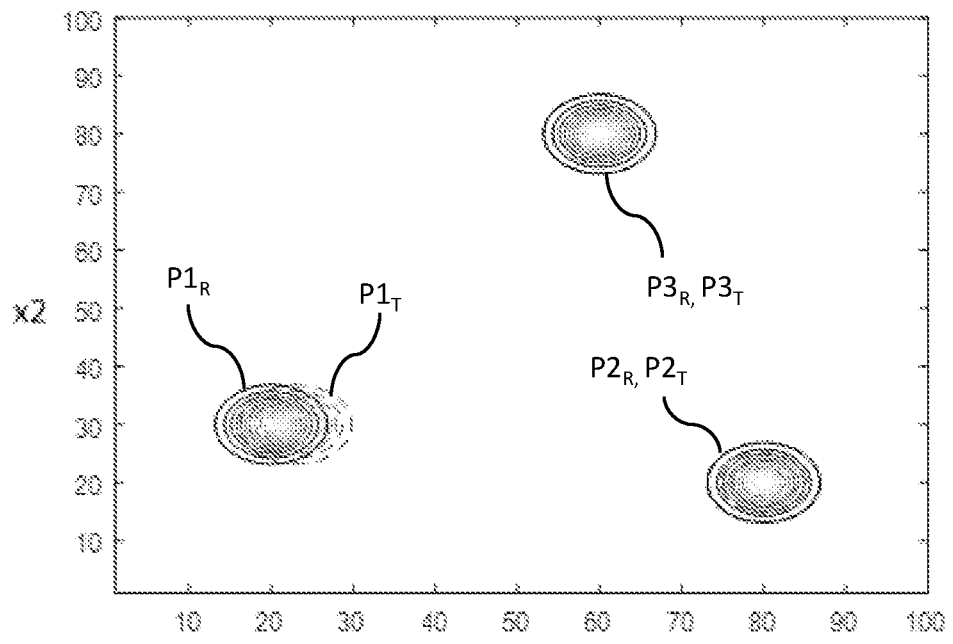
FIG. 4A shows a graphical overlay of the reference and test spectra with highlighting differences between the spectra.
Figure 4B:
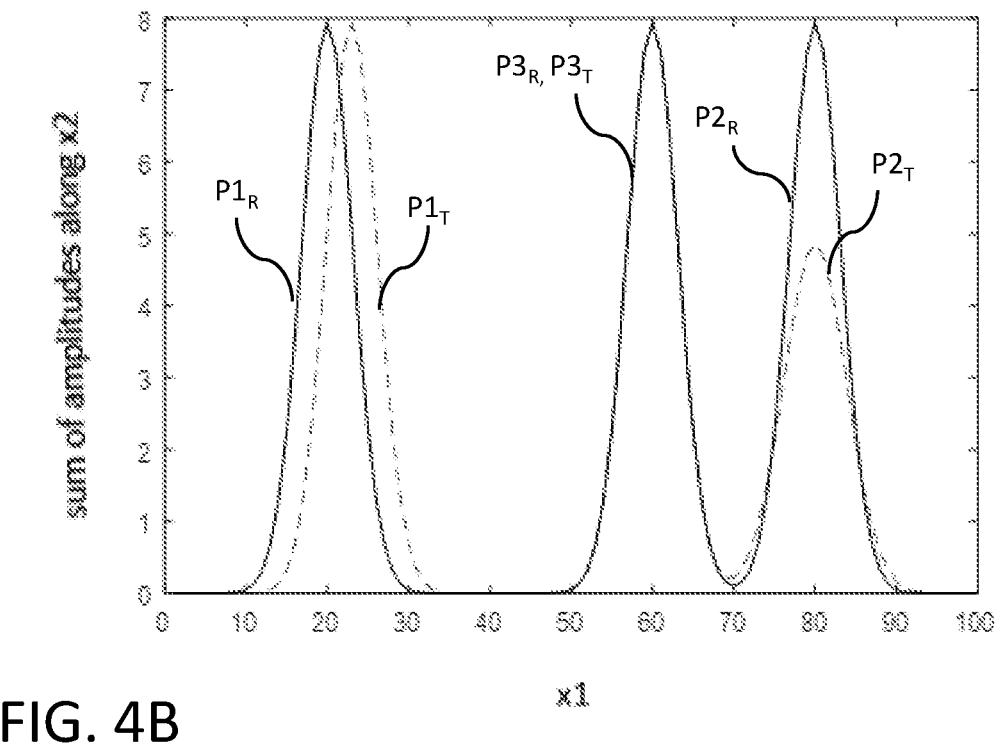
FIG. 4B shows a projection of the overlay graphics illustrating the differences in the amplitudes of respective NMR signal peaks.

FIGS. 4A and 4B show graphical overlays of the reference and test spectrum with highlighting differences between the spectra. Thereby, FIG. 4A is the direct overlay of the spectra shown in FIGS. 3A, 3B, whereas FIG. 4B shows a projection of the overlay graphics in the x1 dimension illustrating the differences in the sum of the amplitudes of the respective NMR signal peaks along the x2 dimension. The shift of $P1_T$ versus $P1_R$ and the broadening of $P2_T$ versus $P2_R$ are clearly visible. As described earlier, the P1 shift relates to a structural change of the test molecule itself in view of the reference molecule, whereas the broadening of P2 is an indicator for a structural change of the environment of the test molecule.

Turning back to FIG. 1A, the SM generator 130 now uses a similarity function (SF) 121 to compute 1330, for the currently processed spectrum point XR, an initial local similarity value 121-1 representing the local similarity between the reference spectrum and the test spectrum within the corresponding similarity regions. A person skilled in the art may use various similarity functions including, but not limited to, a Pearson correlation function, cosine similarity function, Euclidian distance, Manhattan distance, Minkowski distance, local norm ratio.

In one advantageous embodiment, the local similarity LS between corresponding similarity regions in the test and reference spectrum may be determined by a modified cosine similarity function as defined by the following formula F1:

$$LS\{X_R\} = \frac{\sum A_R(X_R) \cdot A_T(X_T)}{\text{Mod}Norm(A_R, A_T)} \tag{F1}$$

wherein $A_R(X_R)$ is the amplitude of the reference spectrum at spectrum point $X_R$ and $A_T(X_T)$ is the amplitude of the test spectrum at spectrum point $X_T$, and the denominator is defined by the formula F2:

$$\text{Mod Norm}(A_R, A_T) = \max[\Sigma(A_R(X_R))^2, \Sigma(A_T(X_T))^2], \tag{F2}$$

and the sums are computed over all equivalent (corresponding) points in the respective similarity regions of the reference spectrum and test spectrum.

In an alternative embodiment, the local similarity between corresponding similarity regions in the test and reference spectrum may be determined by a local norm ratio similarity function where the local norm LN is defined by the following formula F3:

$$LN(X_R) = \sqrt{\frac{\sum (A_R(X_R))^2}{\sum (A_T(X_T))^2}}, \quad (F3)$$

wherein $A_R(X_R)$ is the amplitude of the reference spectrum at point $X_R$ and $A_T(X_T)$ is the amplitude of the test spectrum at point $X_T$, and the sum is carried out over all points in the currently processed reference/test similarity regions.

The local norm ratio LNR is defined as:

$$LNR(X_R) = \frac{\min\left[\sqrt{\frac{\sum (A_R(X_R))^2}{\sum (A_T(X_T))^2}}, \sqrt{\frac{\sum (A_T(X_T))^2}{\sum (A_R(X_R))^2}}\right]}{\max\left[\sqrt{\frac{\sum (A_R(X_R))^2}{\sum (A_T(X_T))^2}}, \sqrt{\frac{\sum (A_T(X_T))^2}{\sum (A_R(X_R))^2}}\right]},$$

wherein $A_R(X_R)$ is the amplitude of the reference spectrum at point $X_R$ and $A_T(X_T)$ is the amplitude of the test spectrum at point $X_T$ and the sum is carried out over all spectrum points in the first or second similarity region.

After having processed a particular spectrum point, a control element 122 of the processing loop 1300 checks if already all selected spectrum points of the subset have been processed. If not, the loop turns to the next spectrum point and repeats the previously described steps. The order in which the spectrum points of the multidimensional spectrum space are processed is not relevant. At the end of the loop, an initial local similarity value 121-1 is available for the processed spectrum points of the subset(s). The plurality of such initial local similarity values 121-1 represent a similarity map SM1 in which contours of a first shape type are indicators I1 for structural changes of the test molecule, and in which contours of a second shape type are indicators I2 for structural changes of the environment of said test molecule in relation to the reference molecule. It is to be noted that the similarity map SM1 includes no contours at all where the reference spectrum shows no differences versus the test spectrum because for such (identical) parts of the spectrum the local similarity is always 1. That is, such part of the spectrum results in a regular plane in the similarity map. The some over the local similarity values of all spectrum points of the subset can be determined as a quantity indicating the intensity distribution similarity of the reference spectrum and the test spectrum.

Figure 5A:
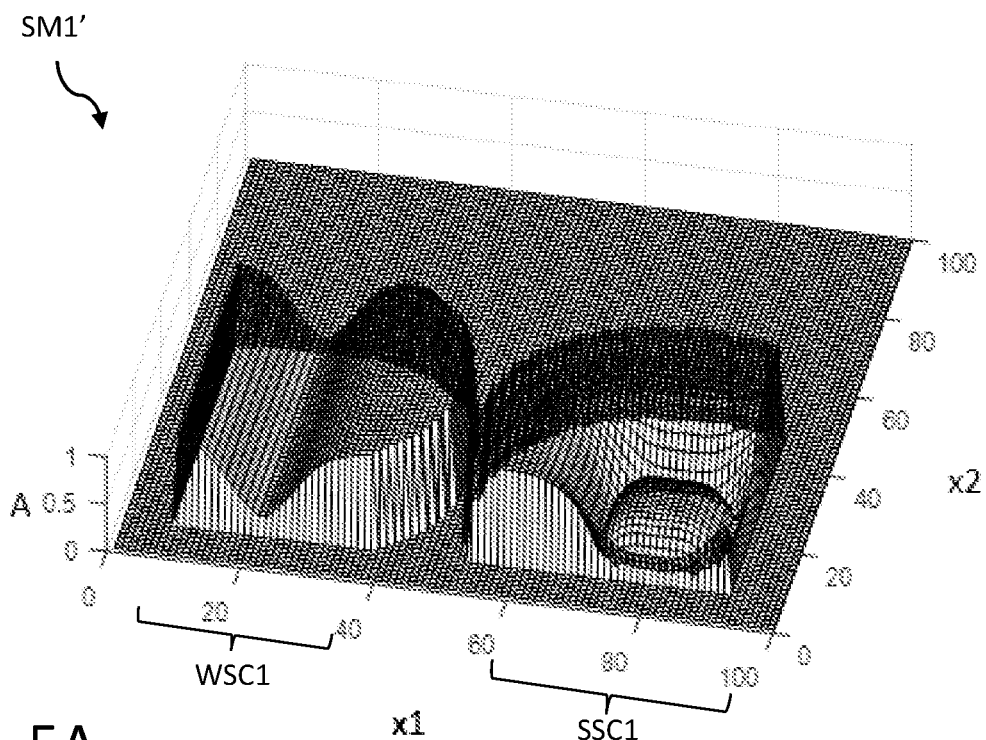
FIGS. 5A, 5B illustrate graphical representations of similarity maps generated according to an embodiment.
Figure 5B:
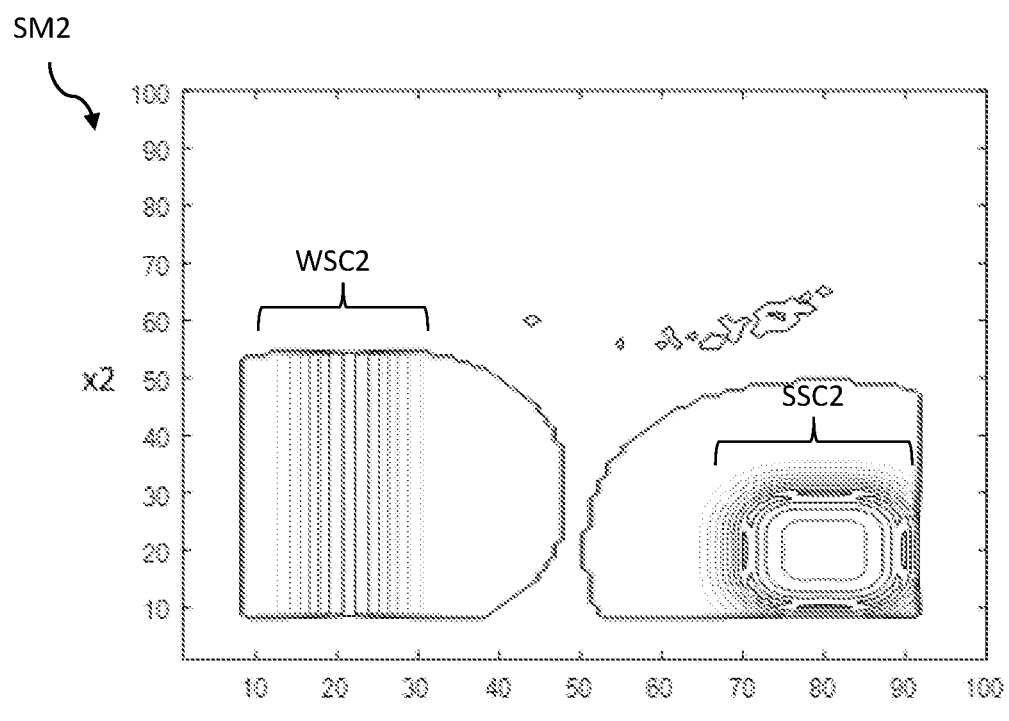

For a convenient visual representation of the similarity map SM1 one may actually show an inverted similarity map SM1' with the inverted initial local similarity values ILSV being: ILSV=1−LSV, with LSV being the respective initial local similarity value. This results in an "inverted" similarity map where all points of the map with identical spectrum portions are zero (because the respective initial local similarity value is "1" for each spectrum point in the respective similarity areas). FIGS. 5A, 5B illustrate such an inverted view SM1' of the similar map obtained by the SM generator for the reference and test spectra illustrated in FIGS. 3A, 3B.

In the inverted similarity map SM1' of FIG. 5A, the contours WSC1 of the first shape type (indicators for structural changes of the test molecule) are wave shaped and clearly visible with values greater than zero. Also in the original similarity map SM1, the contours of the first type are wave shaped. However, waves might not be so clearly visible when being shown on top of the identity plane (similarity=1). In the inverted similarity map SM1' of FIG. 5A, the contours SSC1 of the second shape type (indicators for structural changes of the environment of said test molecule) are sink shaped and clearly visible with values greater than zero. In the original similarity map SM1, the contours of the second type are also sink shaped. However, the sink departs from the similarity=1 plane.

FIG. 5B illustrates an alternative representation SM2 of the similarity map as a two-dimensional projection of the three dimensional representation of FIG. 5A. The wave shaped contours are represented by corresponding level curves WSC2, and the sink shaped contours are represented by corresponding level curves SSC2.

Figure 1B:
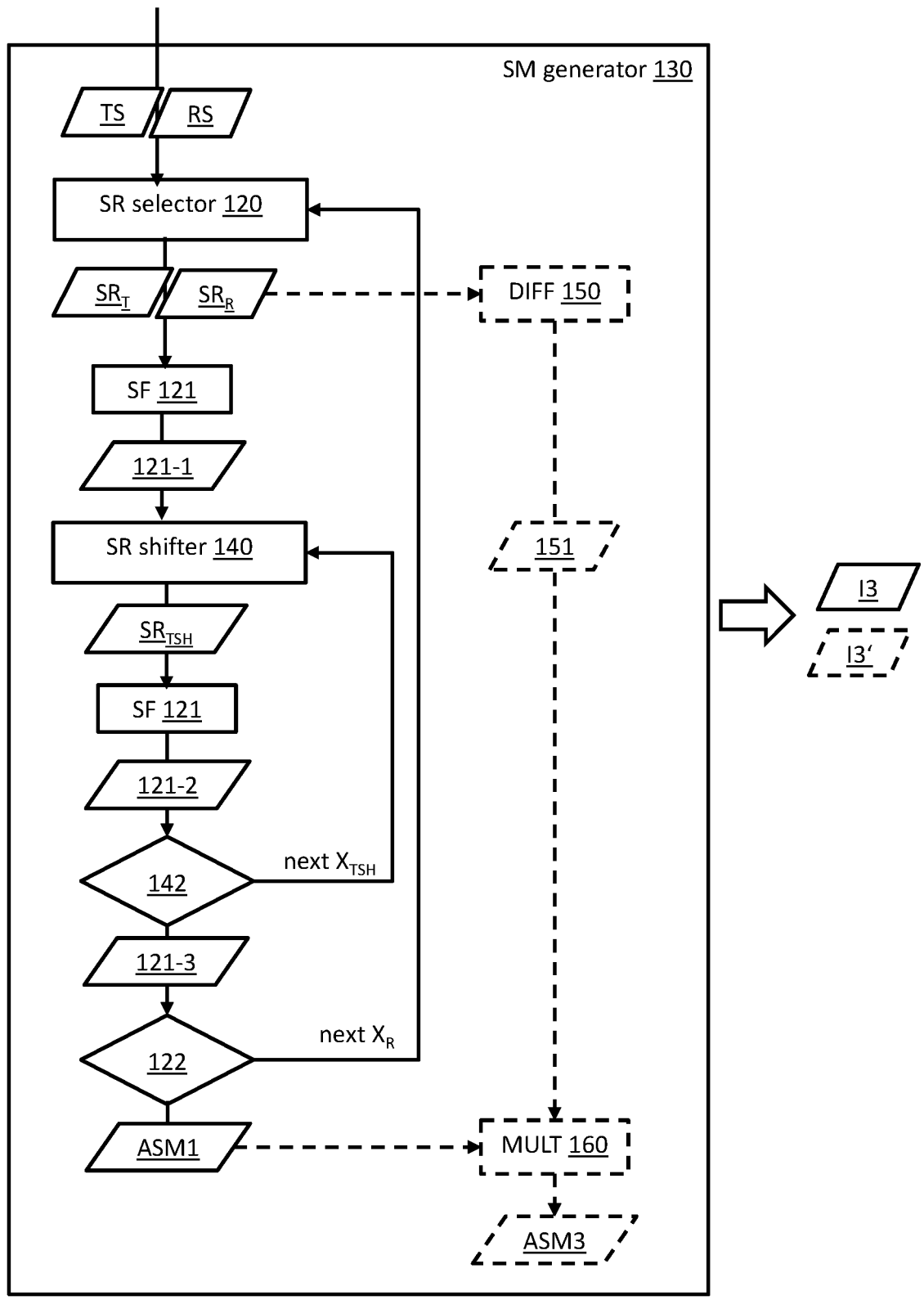
FIGS. 1B, 1C show two alternative embodiments of the similarity map generator module of the computer system.

FIG. 1B illustrates an optional embodiment of the SM generator 130 which can lead to an improved version ASM1 of the similarity map. In this embodiment, the SM generator implements an inner loop inside the outer loop which allows to filter out indicators for peak shifts from the similarity map. That is, the similarity map provided by this SM generator embodiment provides only the indicators for changes that relate to structural changes of the environment of the test molecule and is therefore referred to as environment similarity map. To achieve this, the following steps are implemented by the SM generator as an inner loop which is executed for the currently processed spectrum point (of the outer loop).

Figure 6A:
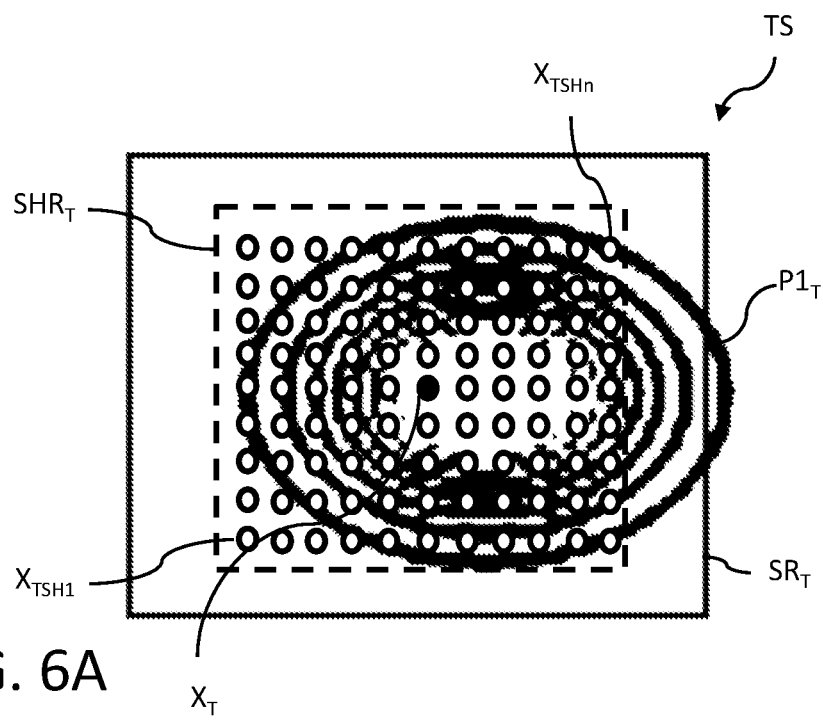
FIG. 6A illustrates an example of a similarity region and a shifting region as defined in the test spectrum.

The inner loop is performed for all spectrum points within a predefined shifting region of the test spectrum. FIG. 6A illustrates an example of a similarity region $SR_T$ and a shifting region $SHR_T$ as defined in the test spectrum TS. The figure illustrates the portion of the test spectrum which includes the shifted peak $P1_T$. The spectrum points within the shifting region $SHR_T$ are represented with circles with the currently processed spectrum point $X_T$ in the centre of the shifting region shown as a black bullet point. The shifting region can have other shapes and sizes but is advantageously located inside the similarity region associated with the currently processed spectrum point. In the example, the lower left spectrum point in the shifting region is $X_{TSH1}$ and the upper right spectrum point is $X_{TSHn}$.

Turning back to FIG. 1B, the following steps are repeated within the inner loop (SR shifter 140) until all spectrum points within the shifting region are processed. The second similarity region $SR_T$ is shifted, during one execution of the inner loop, to a shifted similarity region $SR_{TSH}$ surrounding a further spectrum point $X_{TSH}$ of the shifting region $SHR_T$. The SM generator 130 then computes, by using the similarity function 121, a shifted local similarity value 121-2 representing the local similarity between the reference spectrum in the first similarity region $SR_R$ and the test spectrum in the shifted similarity region $SR_{TSH}$. The control element 142 checks if already all spectrum points within the shifting area were processed by the inner loop. If not, the loop is repeated with a not yet processed spectrum point in the shifting region (next $X_{TSH}$). If yes, the inner loop is finished for the currently processed spectrum point of the outer loop and the SM generator determines the spectrum point within the predefined shifting region showing the maximum shifted local similarity value 121-3. The determined maximum shifted local similarity values represent an environment similarity map ASM1 in which contours of a third shape type are indicators I3 for structural changes of the environment of said test molecule in relation to the reference molecule. Thereby, the indicators for structural changes of the molecule are completely eliminated.

Figure 6B:
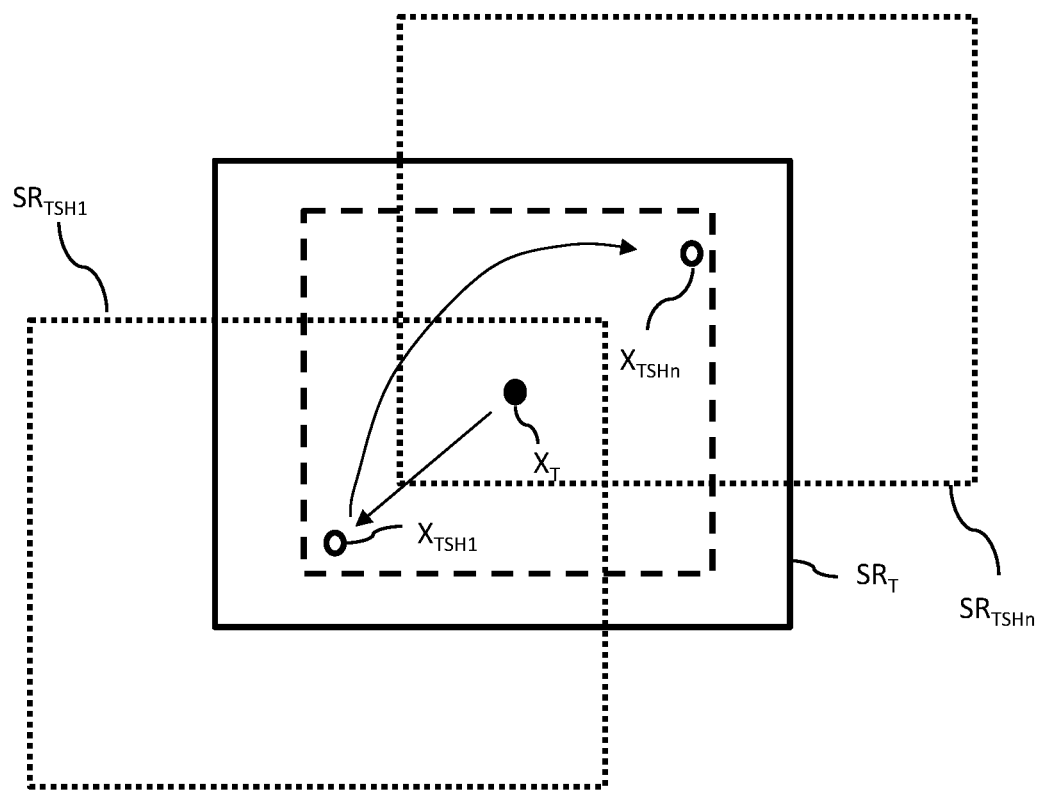
FIG. 6B illustrates examples of shifted similarity regions in the test spectrum.

FIG. 6B illustrates two shifting steps in the inner loop where the similarity region $SR_T$ is initially shifted from $X_T$ to $X_{TSH1}$ resulting the shifted similarity region $SR_{TSH1}$. In a subsequent inner loop iteration the shifted similarity region $SR_{TSH1}$ is shifted to the shifted similarity region $SR_{TSHn}$ which is associated with the spectrum point $X_{TSHn}$ in the shifting region. For each shifted similarity region the corresponding shifted local similarity value is determined until all spectrum points of the shifting region are processed. Finally the maximum value of all determined shifted local similarity values is stored for the currently processed spectrum point of the outer loop before the outer loop proceeds with the next spectrum point in the first similarity region.

In the embodiment of FIG. 1B, the spectrum points of the shifting area may be processed in a predefined order by using a predefined path to navigate through the shifting areas until all spectrum points have been processed therein. In an optional embodiment, the inner loop (SR shifter 140) is not executed for all spectrum points in the shifting region. Rather, an evaluation step is included after the shifted local similarity value has been computed for the current iteration where the computed shifted local similarity value of the current iteration is compared with shifted local similarity value of the previous iteration. If the computed shifted local similarity value of the current iteration is smaller than the one of the previous inner loop iteration, the SR shifter 140 deviates from the predefined order in which the inner loop proceeds through the shifting area by not further pursuing the predefined path. Instead, the SR shifter changes the direction (in the n-dimensional X-space of the spectrum) for selecting the next $X_{TSH}$ until a shifted local similarity value is computed which exceeds the one of the one with the highest value in the previously performed iterations of the inner loop. The change in direction may occur randomly or in accordance with a predefined pattern (e.g., always go to the next not yet processed direct neighbor of the previously processed spectrum point). If no higher shifted local similarity value can be found, the inner loop stops and the shifted local similarity value with the highest value determined in the current iteration of the inner loop is used as the maximum shifted local similarity value for the currently processed spectrum point of the outer loop.

To summarize, the sequence of spectrum points in the shifting region used for shifting the second similarity region for the currently processed spectrum point follows a route of increasing shifted local similarity values. That is, the SR shifter is testing if any of the not yet processed spectrum points in the shifting region in the vicinity of the spectrum point with the currently highest shifted local similarity value is leading to an increase of the similarity value. If not, the inner loop processing stops. Otherwise, a path in the shifting region is pursued which is along spectrum points leading to an increase of the respective similarity values.

In this embodiment, the computation of the inner loop requires typically less computing resources because an iteration of the inner loop stops at the point in time when a local similarity maximum is identified for the currently processed spectrum point. This saves unnecessary computing operations for the remaining spectrum points in the shifting region.

Figure 7A:
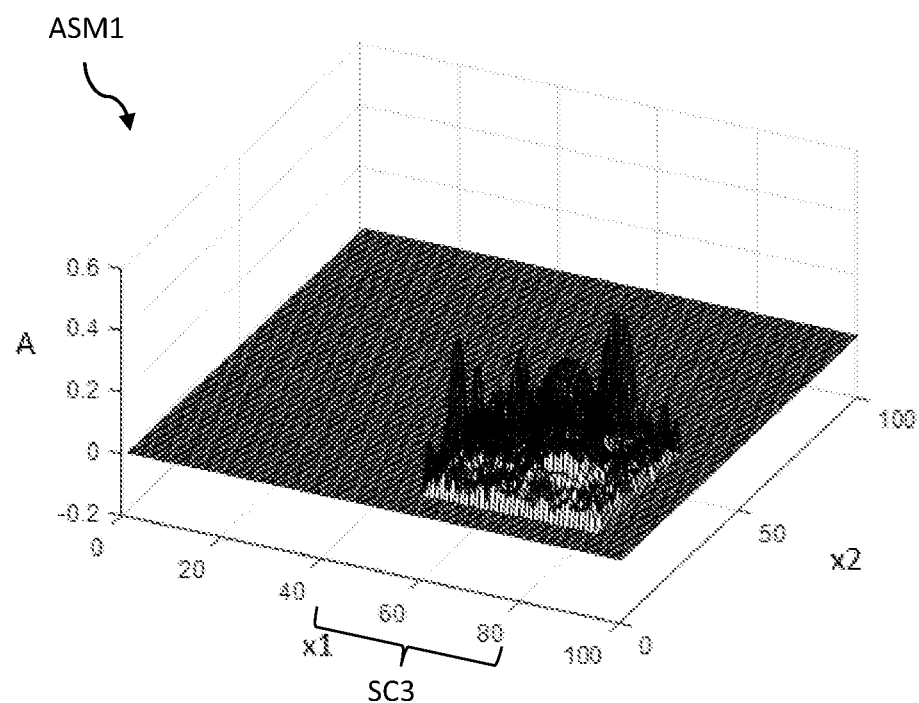
FIGS. 7A, 7B illustrate graphical representations of an example environment similarity map generated in accordance with an embodiment.
Figure 7B:
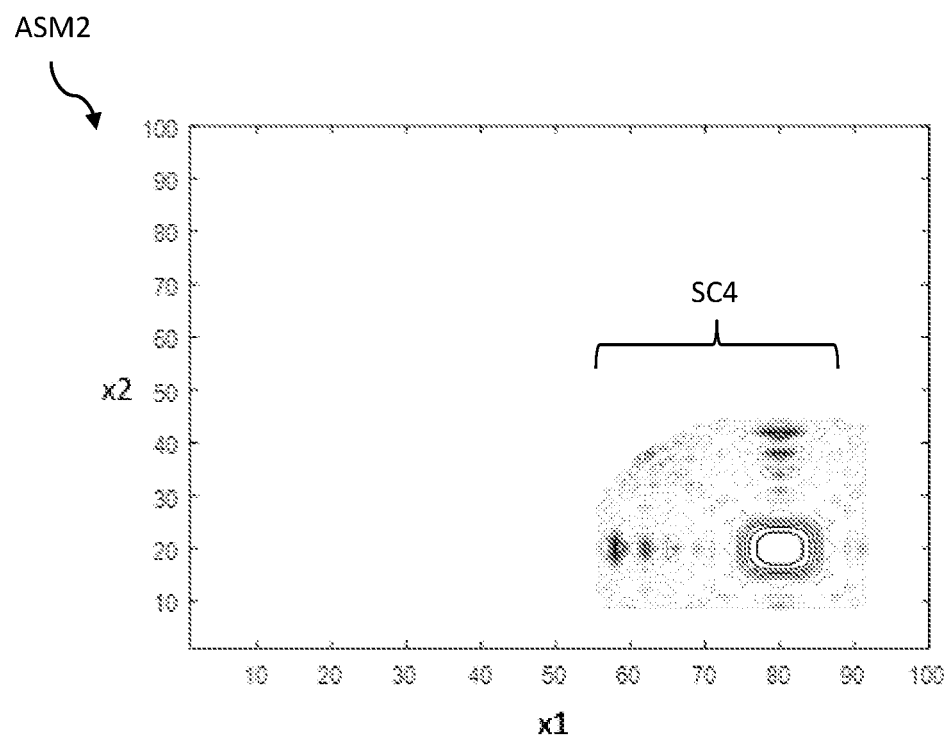

FIGS. 7A, 7B illustrate graphical representations of an example environment similarity map as generated with the embodiment of the SM generator in FIG. 1B. In FIG. 7A, a three dimensional map (inverted) environment similarity map ASM1 is shown which relates to test and reference spectrum as indicated in FIG. 4A. Only indicators for the peak broadening of the peak $P2_T$ are included as represented by the contours of shape contour SC3. All other indicators have been eliminated from the environment similarity map ASM1. FIG. 7B illustrates a two dimensional projection ASM2 of the environment similarity map where indicators for peak broadening are represented by the level curves SC4.

The indicators in FIGS. 7A, 7B still show quite some noise which can be further improved by an embodiment of the SM generator as illustrated in FIB. 1B with using the modules DIFF 150 and MULT 160 illustrated with dashed lines.

The module DIFF 150 computes a spectrum difference value 151 for each spectrum point of the selected subset of spectrum points by computing a difference between respective amplitudes in the reference spectrum and the test spectrum. The module MULT 160 then multiplies the determined maximum shifted local similarity values 121-3 of the environment similarity map ASM1 with the respective spectrum difference values 151 to obtain an improved environment similarity map ASM3 with indicators I3' that allow for more accurate detection of broadened peaks in the test spectrum.

Figure 8A:
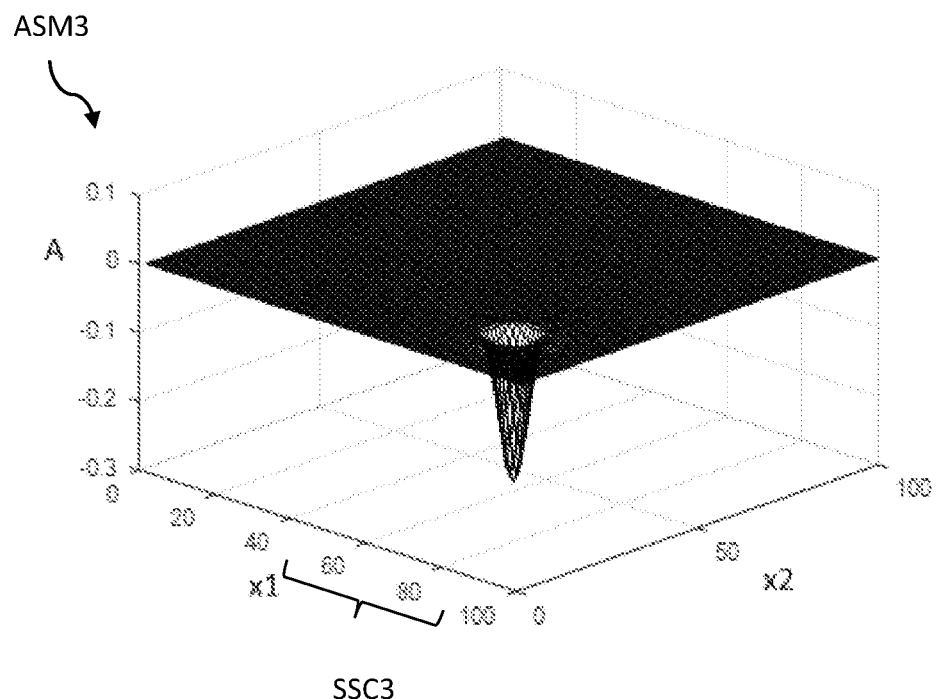
FIGS. 8A, 8B illustrate graphical representation examples of an improved environment similarity map generated in accordance with an embodiment.
Figure 8B:
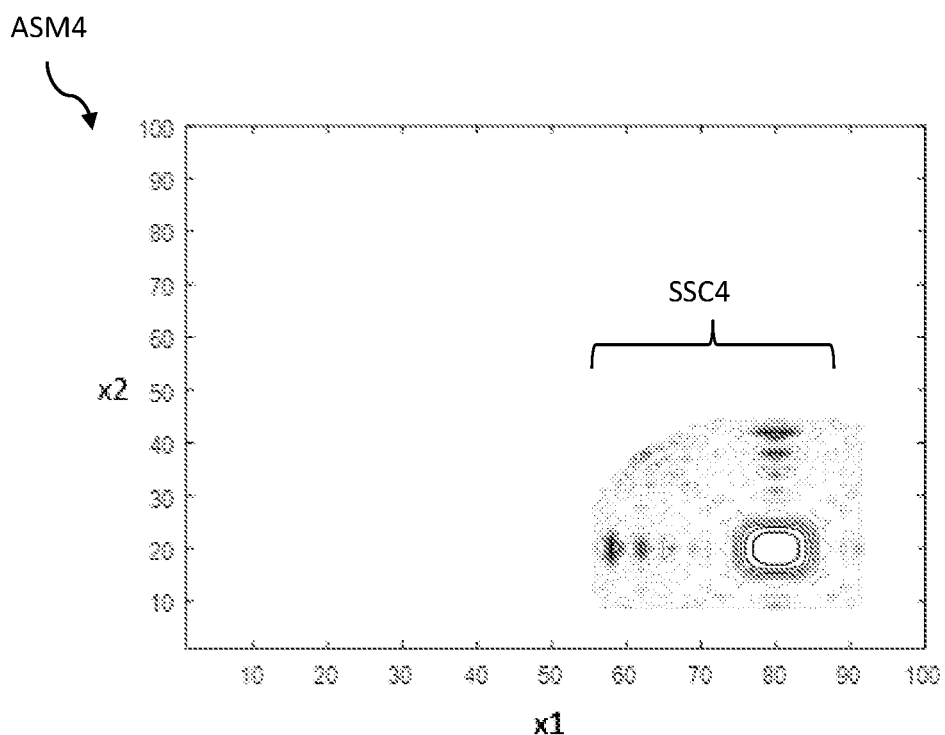

The multiplication of the environment similarity map ASM1 with the difference values (difference spectrum) leads to a suppression of the noise in ASM1. FIGS. 8A, 8B illustrate graphical representation examples ASM3, ASM4 of such an improved (inverted) environment similarity map generated in accordance with this optional embodiment of the SM generator. As can be seen in FIG. 8A, the shape contour of the third shape type is now a very clear sink shaped contour SSC3 which allows to unambiguously identify parts in the test spectrum where peak broadening occurred in relation to the reference spectrum. In other words, such peaks which reflect a structural change of the test molecules' environment are unambiguously identified in the improved environment similarity map. In FIG. 8B, again, a projection ASM4 of ASM3 is shown where the respective contours are the corresponding level curves SSC4.

Figure 1C:
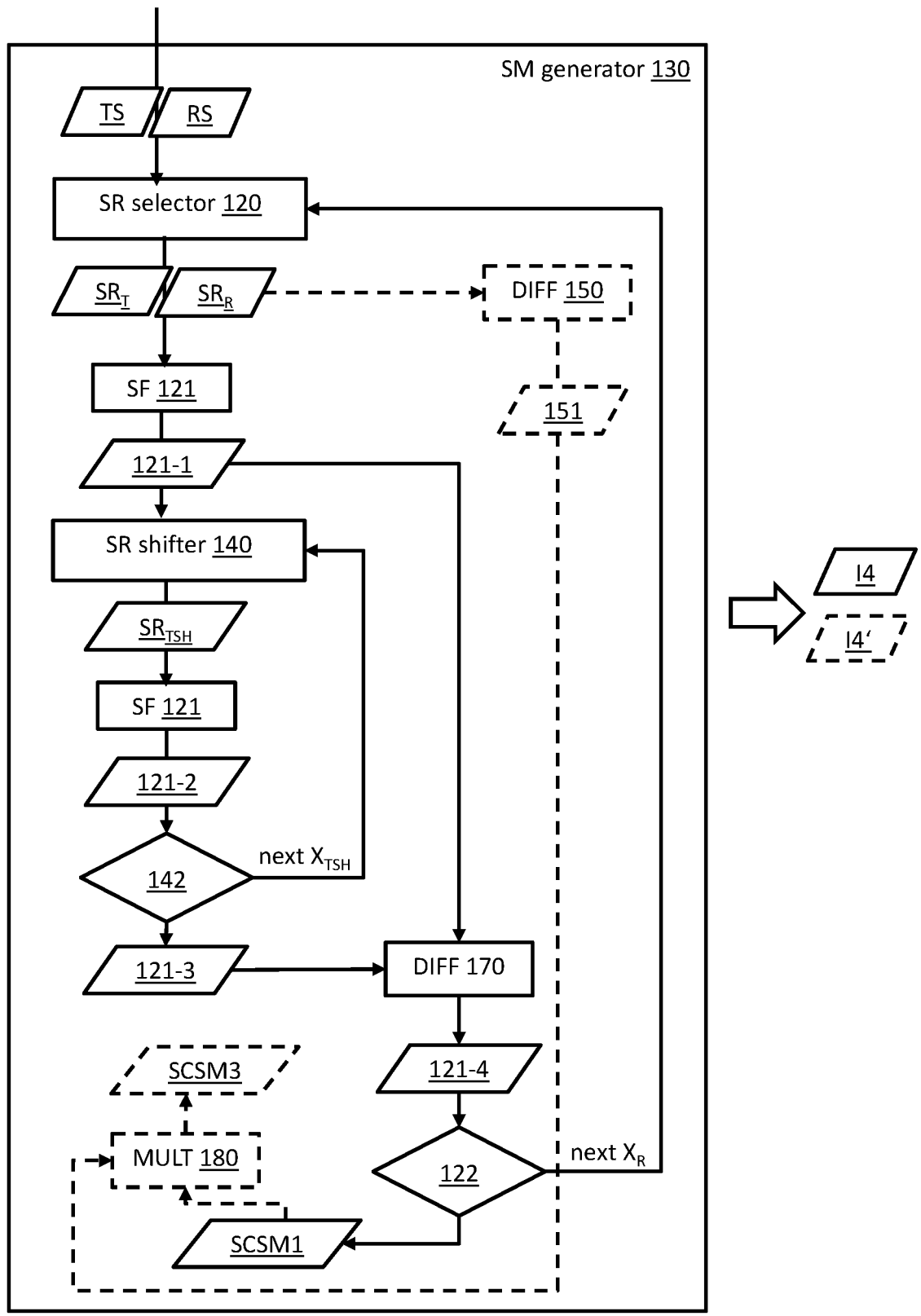

A further embodiment of the SM generator 130 is illustrated in FIG. 1C. This embodiment is building on top of the basic embodiment of FIG. 1B which includes the SR shifter 140 (inner loop). This further embodiment includes a further module DIFF 170. The DIFF module 170 computes a similarity increase value 121-4 for each spectrum point of the subset as the difference between the respective initial local similarity value 121-1 and the respective maximum local shifted similarity value 121-3. Thereby, the similarity increase values represent a structural change similarity map SCSM1 in which contours of the first shape type are indicators I4 for structural change of the test molecule in relation to the reference molecule.

Figure 9A:
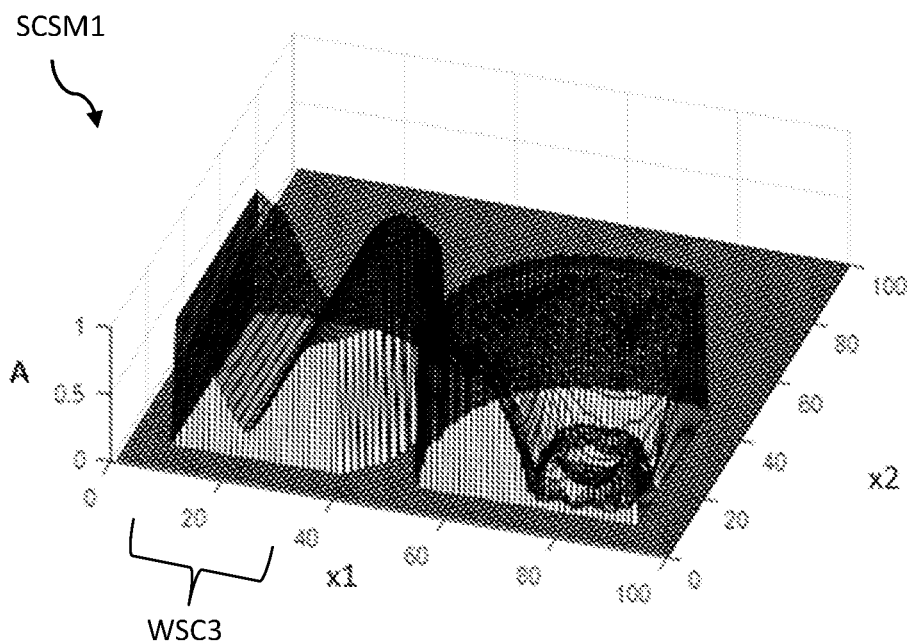
FIGS. 9A, 9B illustrate graphical representation examples of a structural change similarity map generated in accordance with an embodiment.
Figure 9B:
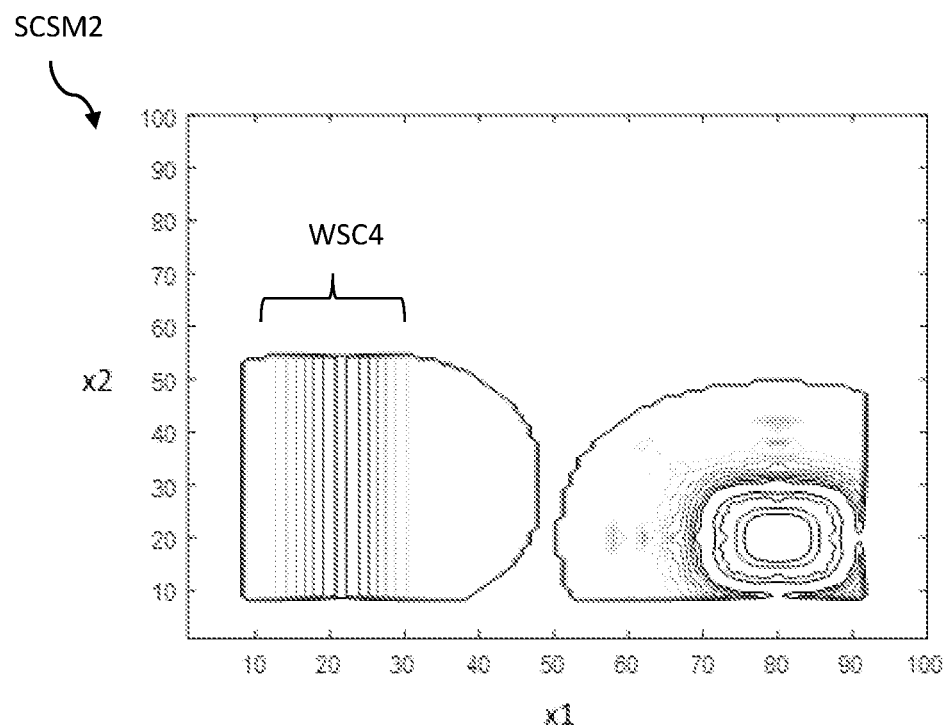

FIGS. 9A, 9B illustrate graphical representation examples SCSM1, SCSM2 of a structural change similarity map generated in accordance with the SM generator embodiment in FIG. 1C. Although in the structural change similarity maps SCSM1 and SCM2 the indicators for the peak broadening are not entirely suppressed, the wave shaped indicators WSC3, WSC4 indicating changes in the structure of the test molecule itself are more clearly defined than in the original similarity maps in FIGS. 5A, 5B.

The structural change similarity maps can be further improved with the optional embodiment shown in FIG. 1C using the further modules DIFF 150 and MULT 180 (with dashed lines). DIFF 150, as already used in the optional embodiment of FIG. 1B, computes the spectrum difference value 151 for each spectrum point of the subset by computing a difference between respective amplitudes in the reference spectrum and the test spectrum. The MULT 180 module multiplies the similarity increase values 121-4 with the respective spectrum difference values 151 to obtain an improved structural change similarity map SCSM3. In this improved structural change similarity map SCSM3, the indicators I4' unambiguously represent peak changes because of the structural changes of the test molecule itself. The improvement is achieved because noise is removed from the similarly map which leads to a substantial reduction of indicators which remained from broadened peaks.

Figure 10A:
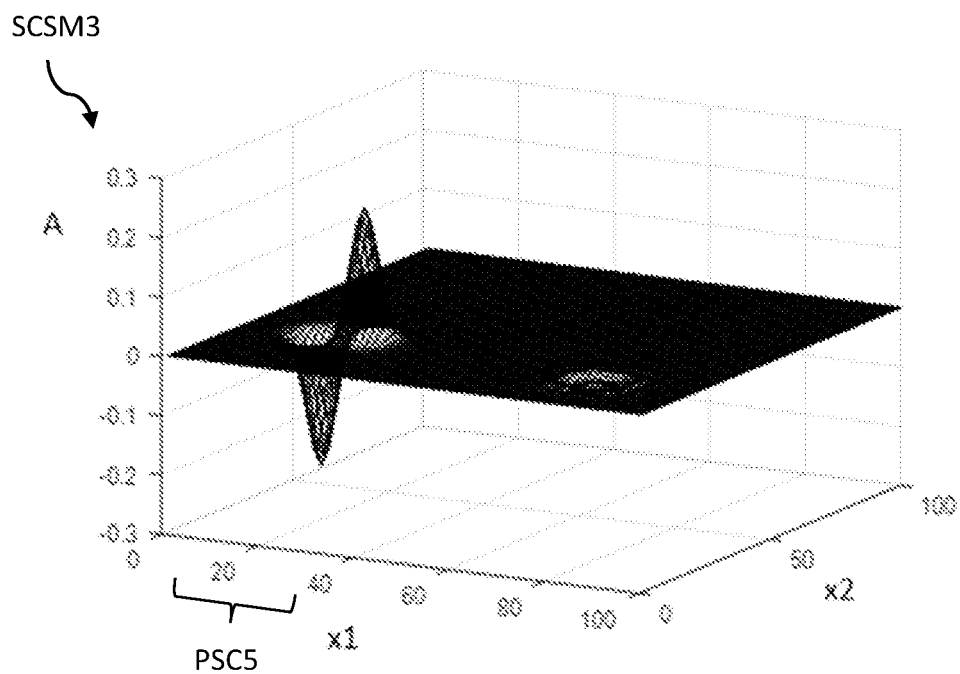
FIGS. 10A, 10B illustrate graphical representation example of an improved structural change similarity map generated in accordance with an embodiment.
Figure 10B:
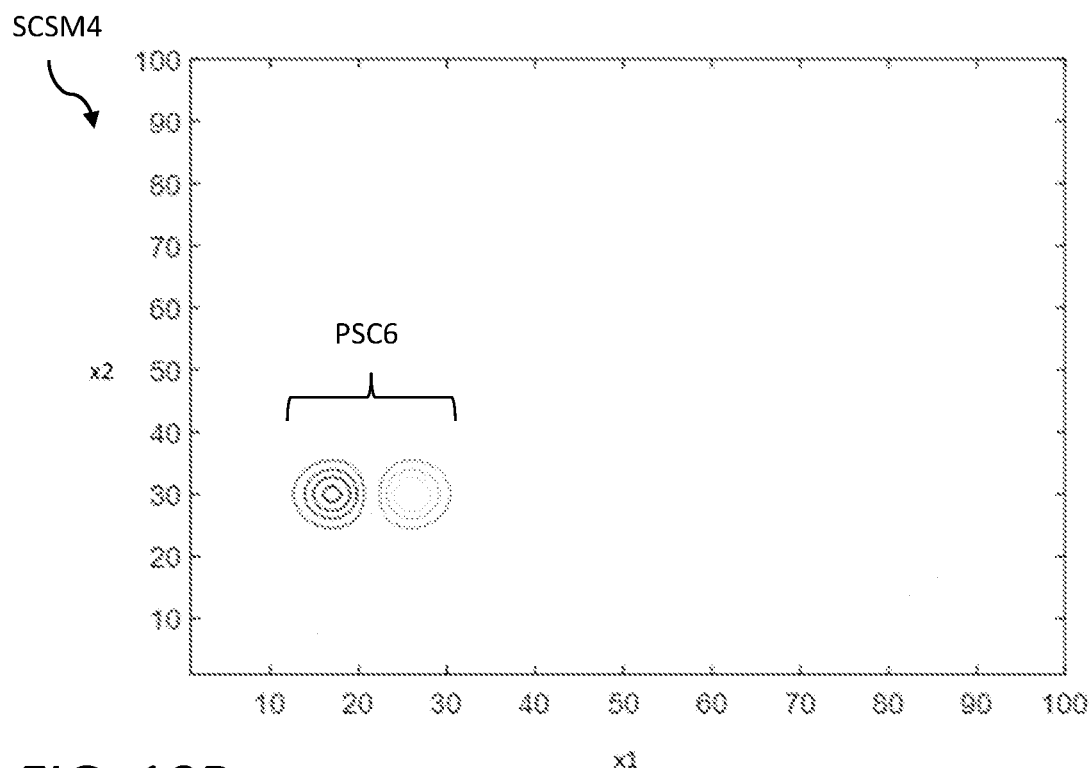

FIGS. 10A, 10B illustrate graphical representation examples SCSM3, SCSM4 of improved structural change similarity maps. In FIG. 10A, the contours PSC5 of the indicators I4' are peak/sink shaped. The position of an original peak in the reference spectrum is indicated by a sink (in the inversed representation of the spectra), and the position of the shifted peak in the test spectrum is indicated by a peak. Such contours are unambiguously detectable because the remaining indicators of the broadened peaks are in the order of the noise level and can therefore not be confused with the indicators for the structural changes of the test molecules. In. FIG. 10B, the peak and sink are illustrated by corresponding level curves PSC6. It is to be noted that in FIG. 10B the threshold for creating a first level curve of a peak/sink exceeds the level of the remaining peak broadening indicators for which reason, in FIG. 10B, such indicators are completely filtered out. As a consequence, this embodiment allows an unambiguous detection of indicators for peak shifts.

Figure 11:
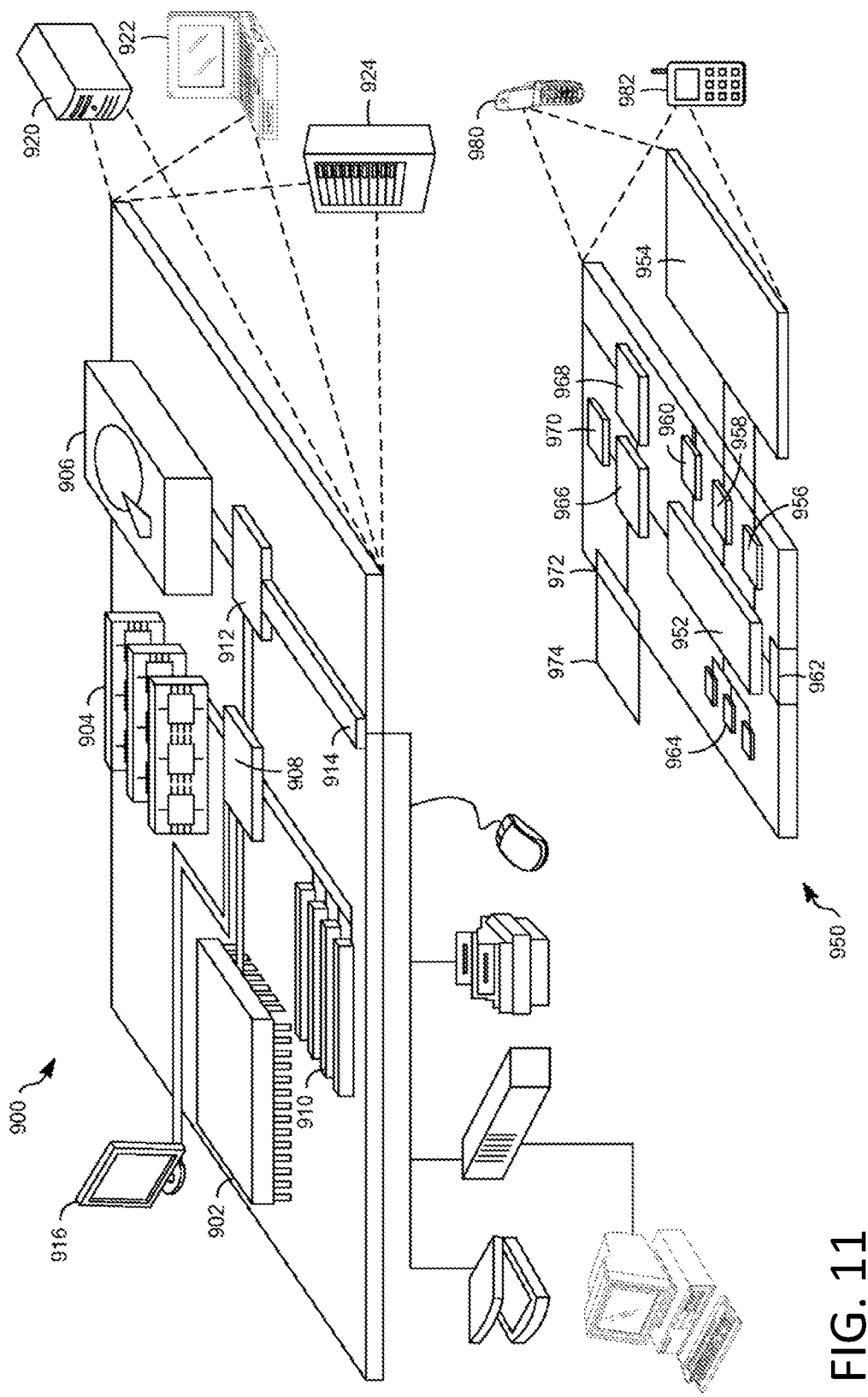
FIG. 11 is a diagram that shows an example of a generic computer device and a generic mobile computer device which may be used with the techniques described herein.

FIG. 11 is a diagram that shows an example of a generic computer device 900 and a generic mobile computer device 950, which may be used with the techniques described here. In some embodiments, computing device 900 may relate to the system 100 (cf. FIG. 1). Computing device 950 is intended to represent various forms of mobile devices, such as personal digital assistants, cellular telephones, smart phones, and other similar computing devices. In the context of this disclosure the computing device 950 may provide the I/O means of FIG. 1. In other embodiments, the entire system 100 may be implemented on the mobile device 950. The components shown here, their connections and relationships, and their functions, are meant to be exemplary only, and are not meant to limit implementations described and/or claimed in this document.

Computing device 900 includes a processor 902, memory 904, a storage device 906, a high-speed interface 908 connecting to memory 904 and high-speed expansion ports 910, and a low speed interface 912 connecting to low speed bus 914 and storage device 906. Each of the components 902, 904, 906, 908, 910, and 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as display 916 coupled to high speed interface 908. In other implementations, multiple processors and/or multiple buses may be used, as appropriate, along with multiple memories and types of memory. Also, multiple computing devices 900 may be connected, with each device providing portions of the necessary operations (e.g., as a server bank, a group of blade servers, or a multi-processor system).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 904, the storage device 906, or memory on processor 902.

The high speed controller 908 manages bandwidth-intensive operations for the computing device 900, while the low speed controller 912 manages lower bandwidth-intensive operations. Such allocation of functions is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 966, and a transceiver 968, among other components. The device 950 may also be provided with a storage device, such as a microdrive or other device, to provide additional storage. Each of the components 950, 952, 964, 954, 966, and 968, are interconnected using various buses, and several of the components may be mounted on a common motherboard or in other manners as appropriate.

The processor 952 can execute instructions within the computing device 950, including instructions stored in the memory 964. The processor may be implemented as a chipset of chips that include separate and multiple analog and digital processors. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD (Thin-Film-Transistor Liquid Crystal Display) or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provide in communication with processor 952, so as to enable near area communication of device 950 with other devices. External interface 962 may provide, for example, for wired communication in some implementations, or for wireless communication in other implementations, and multiple interfaces may also be used.

The memory 964 stores information within the computing device 950. The memory 964 can be implemented as one or more of a computer-readable medium or media, a volatile memory unit or units, or a non-volatile memory unit or units. Expansion memory 984 may also be provided and connected to device 950 through expansion interface 982, which may include, for example, a SIMM (Single In Line Memory Module) card interface. Such expansion memory 984 may provide extra storage space for device 950, or may also store applications or other information for device 950. Specifically, expansion memory 984 may include instructions to carry out or supplement the processes described above, and may include secure information also. Thus, for example, expansion memory 984 may act as a security module for device 950, and may be programmed with instructions that permit secure use of device 950. In addition, secure applications may be provided via the SIMM cards, along with additional information, such as placing the identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 984, or memory on processor 952, that may be received, for example, over transceiver 968 or external interface 962.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 968. In addition, short-range communication may occur, such as using a Bluetooth, WiFi, or other such transceiver (not shown). In addition, GPS (Global Positioning System) receiver module 980 may provide additional navigation- and location-related wireless data to device 950, which may be used as appropriate by applications running on device 950.

Device 950 may also communicate audibly using audio codec 960, which may receive spoken information from a user and convert it to usable digital information. Audio codec 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smart phone 982, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing device that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing device can include clients and servers. A client and server are generally remote from each other and typically interact through a communication network. The relationship of client and server arises by virtue of computer programs running on the respective computers and having a client-server relationship to each other.

The invention claimed is:

1. A computer-implemented method for detecting indicators for structural changes of NMR active test molecules in a test sample, and detecting indicators for structural changes of the environment of said test molecules in relation to a reference molecule, the method comprising:

obtaining an n-dimensional NMR reference spectrum (RS) associated with the reference molecule having a known spatial structure;

obtaining an n-dimensional NMR test spectrum (TS) associated with the test molecule having an unknown spatial structure, wherein the reference spectrum (RS) and the test spectrum (TS) have the same spectral resolution and the same spectral range so that each spectrum point of the reference spectrum (RS) has a corresponding spectrum point in the test spectrum (TS), with the corresponding spectrum points ($X_R$, $X_T$) having the same coordinates ($x_1$, $x_2$);

processing, for at least a subset of spectrum points of the reference spectrum (RS), the following operations:

selecting, in the reference spectrum (RS), a first similarity region ($SR_R$) surrounding the currently processed spectrum point ($X_R$), and selecting, in the test spectrum (TS), a corresponding second similarity region ($SR_T$) surrounding the corresponding spectrum point ($X_T$) in the test spectrum (TS) and covering the same spectrum points as the first similarity region;

computing, for the currently processed spectrum point ($X_R$), by using a similarity function, an initial local similarity value representing the local similarity between the reference spectrum and the test spectrum within the corresponding similarity regions ($SR_R$, $SR_T$);

wherein the initial local similarity values represent a similarity map (SM1, SM2) in which contours (WSC1, SSC1) of a first shape type are indicators (I1) for structural changes of the test molecule, and in which contours (WSC2, SSC2) of a second shape type are indicators (I2) for structural changes of the environment of said test molecule in relation to the reference molecule; and displaying the indicators (I1) for structural changes of the test molecule with wave-shaped contours, and displaying the indicators (I2) for structural changes of the environment of said test molecule in relation to the reference molecule with sink-shaped or peak-shaped contours, wherein the wave-shaped contours reflect shifted NMR signal peaks of the test spectrum when compared with the reference spectrum such that peaks having disappeared in the test spectrum, as well as peaks only appearing in the test spectrum, remain visible via the displayed wave-shaped contours.

2. The method of claim 1, wherein the processing for the currently processed spectrum point $X_R$ further comprises:

for spectrum points ($X_{TSH1}$ to $X_{TSHn}$) within a predefined shifting region ($SHR_T$) of the test spectrum (TS), shifting the second similarity region ($SR_T$) to a further spectrum point ($X_{TSH1}$, $X_{TSHn}$) of the shifting region ($SHR_T$);

computing, by using the similarity function (121), a shifted local similarity value representing the local similarity between the reference spectrum in the first similarity region ($SR_R$) and the test spectrum in the shifted similarity region ($SR_{TSH1}$, $SR_{TSHn}$); and determining the spectrum point within the predefined shifting region showing the maximum shifted local similarity value;

wherein the determined maximum shifted local similarity values represent an environment similarity map (ASM1, ASM2) in which contours (SC3, SC4) of a third shape type are indicators (I3) for structural changes of the environment of said test molecule in relation to the reference molecule, and indicators for structural changes of the molecule are eliminated.

3. The method of claim 2, further comprising:

computing a spectrum difference value for each spectrum point of the subset by computing a difference between respective amplitudes in the reference spectrum and the test spectrum; and multiplying the determined maximum shifted local similarity values with the respective spectrum difference values to obtain an improved environment similarity map (ASM3, ASM4).

4. The method of claim 2, further comprising:

computing a similarity increase value for each spectrum point of the subset as the difference between the respective initial local similarity value and the respective maximum local shifted similarity value;

wherein the similarity increase values represent a structural change similarity map (SCSM1, SCSM2) in which contours (WSC3, WSC4) of the first shape type are indicators (I4) for structural change of the test molecule in relation to the reference molecule.

5. The method of claim 4, further comprising:

computing a spectrum difference value for each spectrum point of the subset by computing a difference between respective amplitudes in the reference spectrum and the test spectrum; and multiplying the similarity increase values with the respective spectrum difference values to obtain an improved structural change similarity map (SCSM3, SCSM4).

6. The method of claim 1, wherein the size of a particular similarity region is chosen so that the similarity region has an overlap with a particular NMR signal peak in the reference spectrum in the order of the full width half maximum of the particular peak in each dimension of the peak.

7. The method of claim 1, wherein the similarity function is one of a Pearson correlation function, cosine similarity function, Euclidian distance, Manhattan distance, Minkowski distance, local norm ratio.

8. The method of claim 1, wherein the local similarity values LS are computed by a modified cosine similarity function as defined by the formula:

$$LS(X_R, X_T) = \frac{\sum A_R(X_R) \cdot A_T(X_T)}{\text{Mod}Norm(A_R, A_T)}$$

wherein $A_R(X_R)$ is the amplitude of the reference spectrum at spectrum point $X_R$ and $A_T(X_T)$ is the amplitude of the test spectrum at spectrum point $X_T$, and $$\text{Mod Norm} = \max[\Sigma(A_R(X_R))^2, \Sigma(A_T(X_T))^2],$$

and the sum is computed over all equivalent points in the respective similarity regions of the reference spectrum and test spectrum.

9. The method according to claim 4, wherein the sum over the similarity increase values for all spectrum points in the reference spectrum is determined as a quantity representing a global similarity of the entire reference spectrum and the entire test spectrum.

10. The method according to claim 2, wherein the sequence of spectrum points in the shifting region used for shifting the second similarity region for the currently processed spectrum point follows a route of increasing shifted local similarity values.

11. The method according to claim 1, wherein the method is carried out with a set of reference spectra of the same sample molecule in different known spatial structures.

12. A computer system for detecting indicators for structural changes of NMR active test molecules in a test sample, and indicators for structural changes of the environment of said test molecules in relation to a reference molecule, the system comprising:
an interface component adapted to obtain an n-dimensional NMR reference spectrum (RS) associated with the reference molecule having a known spatial structure, and to obtain an n-dimensional NMR test spectrum (TS) associated with the test molecules having an unknown spatial structure, wherein the reference spectrum (RS) and the test spectrum (TS) have the same spectral resolution and the same spectral range so that each spectrum point of the reference spectrum (RS) has a corresponding spectrum point in the test spectrum (TS), with the corresponding spectrum points $(X_R, X_T)$ having the same coordinates $(x_1, x_2)$;
a similarity map generator module adapted to process, for at least a subset of spectrum points of the reference spectrum (RS), the following operations:
selecting, in the reference spectrum (RS), a first similarity region $(SR_R)$ surrounding the currently processed spectrum point $(X_R)$, and selecting, in the test spectrum (TS), a corresponding second similarity region $(SR_T)$ surrounding the corresponding spectrum point $(X_T)$ in the test spectrum (TS) and covering the same spectrum points as the first similarity region;
computing, for the currently processed spectrum point $(X_R)$, by using a similarity function, an initial local similarity value representing the local similarity between the reference spectrum and the test spectrum within the corresponding similarity regions $(SR_R, SR_T)$;
wherein the initial local similarity values represent a similarity map (SM1, SM2) in which contours (WSC1, SSC1) of a first shape type are indicators (I1) for structural changes of the test molecule, and in which contours (WSC2, SSC2) of a second shape type are indicators (I2) for structural changes of the environment of said test molecule in relation to the reference molecule; and
a display displaying the indicators (I1) for structural changes of the test molecule with wave-shaped contours, and displaying the indicators (I2) for structural changes of the environment of said test molecule in relation to the reference molecule with sink-shaped or peak-shaped contours, wherein the wave-shaped contours reflect shifted NMR signal peaks of the test spectrum when compared with the reference spectrum such that peaks having disappeared in the test spectrum, as well as peaks only appearing in the test spectrum, remain visible via the displayed wave-shaped contours.

13. The system of claim 12, wherein the similarity map generator module is further adapted to process, for the currently processed spectrum point $X_R$, the following operations:
for all spectrum points $(X_{TSH1}$ to $X_{TSHn})$ within a predefined shifting region $(SHR_T)$ of the test spectrum (TS),
shifting the second similarity region $(SR_T)$ to a further spectrum point $(X_{TSH1}, X_{TSHn})$ of the shifting region $(SHR_T)$;
computing, by using the similarity function (121), a shifted local similarity value representing the local similarity between the reference spectrum in the first similarity region $(SR_R)$ and the test spectrum in the shifted similarity region $(SR_{TSH1}, SR_{TSHn})$;
determining the spectrum point within the predefined shifting region showing the maximum shifted local similarity value;
wherein the determined maximum shifted local similarity values represent an environment similarity map (ASM1, ASM2) in which contours (SC3, SC4) of a third shape type are indicators (I3) for structural changes of the environment of said test molecule in relation to the reference molecule, and indicators for structural changes of the molecule are eliminated.

14. The system of claim 13, wherein the similarity map generator module is further adapted to process, for the currently processed spectrum point $X_R$, the following operations:
computing a similarity increase value for each spectrum point of the subset as the difference between the respective initial local similarity value and the respective maximum local shifted similarity value;
wherein the similarity increase values represent a structural change similarity map (SCSM1, SCSM2) in which contours (WSC3, WSC4) of the first shape type are indicators (I4) for structural change of the test molecule in relation to the reference molecule.

15. A non-transitory computer readable media storing a program for detecting indicators for structural changes of NMR active test molecules in a test sample, and detecting indicators for structural changes of the environment of said test molecules in relation to a reference molecule, the program comprising instructions that when loaded into a memory of a computer system and being executed by at least one processor of the computer system cause the computer system to:
obtain an n-dimensional NMR reference spectrum (RS) associated with the reference molecule having a known spatial structure;
obtain an n-dimensional NMR test spectrum (TS) associated with the test molecule having an unknown spatial structure, wherein the reference spectrum (RS) and the test spectrum (TS) have the same spectral resolution and the same spectral range so that each spectrum point of the reference spectrum (RS) has a corresponding spectrum point in the test spectrum (TS), with the corresponding spectrum points $(X_R, X_T)$ having the same coordinates $(x_1, x_2)$;
process, for at least a subset of spectrum points of the reference spectrum (RS), the following operations:
selecting, in the reference spectrum (RS), a first similarity region $(SR_R)$ surrounding the currently processed spectrum point $(X_R)$, and selecting, in the test spectrum (TS), a corresponding second similarity region $(SR_T)$ surrounding the corresponding spectrum point ($X_T$) in the test spectrum (TS) and covering the same spectrum points as the first similarity region;

computing, for the currently processed spectrum point ($X_R$), by using a similarity function, an initial local similarity value representing the local similarity between the reference spectrum and the test spectrum within the corresponding similarity regions ($SR_R$, $SR_T$);

wherein the initial local similarity values represent a similarity map (SM1, SM2) in which contours (WSC1, SSC1) of a first shape type are indicators (I1) for structural changes of the test molecule, and in which contours (WSC2, SSC2) of a second shape type are indicators (I2) for structural changes of the environment of said test molecule in relation to the reference molecule; and display the indicators (I1) for structural changes of the test molecule with wave-shaped contours, and displaying the indicators (I2) for structural changes of the environment of said test molecule in relation to the reference molecule with sink-shaped or peak-shaped contours, wherein the wave-shaped contours reflect shifted NMR signal peaks of the test spectrum when compared with the reference spectrum such that peaks having disappeared in the test spectrum, as well as peaks only appearing in the test spectrum, remain visible via the displayed wave-shaped contours.

16. The non-transitory computer readable media of claim 15, wherein the processing for the currently processed spectrum point $X_R$ further comprises:

for spectrum points ($X_{TSH1}$ to $X_{TSHn}$) within a predefined shifting region ($SHR_T$) of the test spectrum (TS), shifting the second similarity region ($SR_T$) to a further spectrum point ($X_{TSH1}$, $X_{TSHn}$) of the shifting region ($SHR_T$);

computing, by using the similarity function (121), a shifted local similarity value representing the local similarity between the reference spectrum in the first similarity region ($SR_R$) and the test spectrum in the shifted similarity region ($SR_{TSH1}$, $SR_{TSHn}$); and determining the spectrum point within the predefined shifting region showing the maximum shifted local similarity value;

wherein the determined maximum shifted local similarity values represent an environment similarity map (ASM1, ASM2) in which contours (SC3, SC4) of a third shape type are indicators (I3) for structural changes of the environment of said test molecule in relation to the reference molecule, and indicators for structural changes of the molecule are eliminated.

17. The non-transitory computer readable media of claim 16, wherein the instructions, when loaded into the memory of the computer system and executed by at least one processor of the computer system, cause the computer system to:

compute a spectrum difference value for each spectrum point of the subset by computing a difference between respective amplitudes in the reference spectrum and the test spectrum; and multiply the determined maximum shifted local similarity values with the respective spectrum difference values to obtain an improved environment similarity map (ASM3, ASM4).

18. The non-transitory computer readable media of claim 16, wherein the instructions, when loaded into the memory of the computer system and executed by at least one processor of the computer system, cause the computer system to:

compute a similarity increase value for each spectrum point of the subset as the difference between the respective initial local similarity value and the respective maximum local shifted similarity value;

wherein the similarity increase values represent a structural change similarity map (SCSM1, SCSM2) in which contours (WSC3, WSC4) of the first shape type are indicators (I4) for structural change of the test molecule in relation to the reference molecule.

19. The non-transitory computer readable media of claim 16, wherein the instructions, when loaded into the memory of the computer system and executed by at least one processor of the computer system, cause the computer system to:

compute a spectrum difference value for each spectrum point of the subset by computing a difference between respective amplitudes in the reference spectrum and the test spectrum; and multiply the similarity increase values with the respective spectrum difference values to obtain an improved structural change similarity map (SCSM3, SCSM4).

20. The non-transitory computer readable media of claim 15, wherein the size of a particular similarity region is chosen so that the particular similarity region has an overlap with a particular NMR signal peak in the reference spectrum in the order of the full width half maximum of the particular peak in each dimension of the peak.

* * * * *